US012691287B2

(12) United States Patent
Prutchi et al.

(10) Patent No.: US 12,691,287 B2
(45) Date of Patent: Jul. 28, 2026

(54) LEAD POSITIONING FOR AN IMPLANTABLE PULSE GENERATOR

(71) Applicant: Impulse Dynamics NV, Willemstad (CW)

(72) Inventors: David Prutchi, Voorhees, NJ (US); Tamir Ben David, Tel-Aviv (IL)

(73) Assignee: Impulse Dynamics NV, Willemstad (NL)

( * ) Notice: Subject to any disclaimer, the term of this patent is extended or adjusted under 35 U.S.C. 154(b) by 255 days.

(21) Appl. No.: 18/039,492

(22) PCT Filed: Mar. 29, 2022

(86) PCT No.: PCT/IB2022/052878
§ 371 (c)(1),
(2) Date: May 31, 2023

(87) PCT Pub. No.: WO2022/208339
PCT Pub. Date: Oct. 6, 2022

(65) Prior Publication Data
US 2024/0001127 A1 Jan. 4, 2024

Related U.S. Application Data

(60) Provisional application No. 63/167,192, filed on Mar. 29, 2021.

(51) Int. Cl.
*A61N 1/365* (2006.01)
*A61N 1/05* (2006.01)
(Continued)

(52) U.S. Cl.
CPC ....... *A61N 1/36585* (2013.01); *A61N 1/3627* (2013.01); *A61N 1/36842* (2017.08); *A61N 1/3686* (2013.01); *A61N 1/37258* (2013.01)

(58) Field of Classification Search
CPC .............. A61N 1/0563; A61N 1/36182; A61N 1/36185; A61N 1/3627; A61N 1/365; A61N 1/36507; A61N 1/36585; A61N 1/36842
See application file for complete search history.

(56) References Cited

U.S. PATENT DOCUMENTS

| | | | |
|---|---|---|---|
| 2009/0030471 A1* | 1/2009 | Rousso | A61N 1/36514 607/27 |
| 2009/0099618 A1* | 4/2009 | Rousso | A61N 1/368 607/9 |

(Continued)

FOREIGN PATENT DOCUMENTS

| | | |
|---|---|---|
| CN | 1787850 | 6/2006 |
| JP | 2010-540076 | 12/2010 |

(Continued)

OTHER PUBLICATIONS

International Preliminary Report on Patentability Dated Oct. 12, 2023 From the International Bureau of WIPO Re. Application No. PCT/IB2022/052878 (9 Pages).

(Continued)

*Primary Examiner* — Brian T Gedeon

(57) ABSTRACT

A method of cardiac signal processing including: receiving measurements from at least two electrodes positioned within the heart; determining, using the measurements, relative positioning of the at least two electrodes relative to each other; evaluating suitability of the relative positioning of the at least two electrodes for measurement of cardiac activity to determine which cardiac cycles should receive cardiac contractility modulation stimulation.

25 Claims, 8 Drawing Sheets

(51) Int. Cl.
    *A61N 1/362*          (2006.01)
    *A61N 1/368*          (2006.01)
    *A61N 1/372*          (2006.01)

(56)               References Cited

U.S. PATENT DOCUMENTS

| | | |
|---|---|---|
| 2013/0030312 A1 | 1/2013 | Keel et al. |
| 2020/0316387 A1 | 10/2020 | Muller et al. |

FOREIGN PATENT DOCUMENTS

| | | |
|---|---|---|
| WO | WO 2020/152619 | 7/2020 |
| WO | WO 2021/079316 | 4/2021 |
| WO | WO 2021/079319 | 4/2021 |
| WO | WO 2022/208339 | 10/2022 |

OTHER PUBLICATIONS

International Search Report and the Written Opinion Dated Jul. 21, 2022 From the International Searching Authority Re. Application No. PCT/IB2022/052878. (17 Pages).

Notice of Reason(s) for Rejection Dated Nov. 11, 2025 From the Japan Patent Office Re. Application No. 2023-555655 and Its Translation Into English. (11 Pages).

Communication Pursuant to Article 94(3) EPC Dated Dec. 23, 2025 From the European Patent Office Re. Application No. 22716495.1 (5 Pages).

\* cited by examiner

100

120 →

MEMORY
130

POWER SUPPLY
124

122

CONTROLLER
126

TRANSMITTER
128

138

RA

LV

116

136

132   144   142

106a

104

134

102

106

108

140

RV 103   105   110   110a

| Measure cardiac electrical activity using cardiac electrodes | 200 |
| Evaluate position of electrodes, using measurements | 202 |

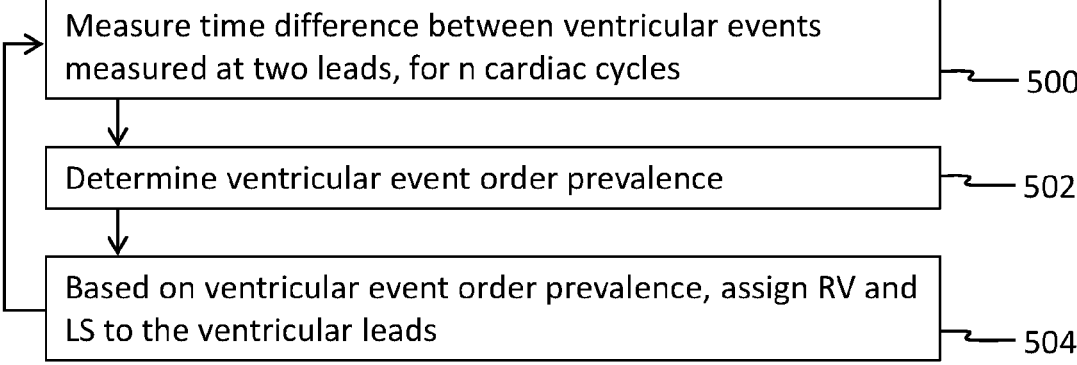

| Measure time difference between ventricular events measured at two leads, for n cardiac cycles | — 500 |

Determine ventricular event order prevalence — 502

Based on ventricular event order prevalence, assign RV and LS to the ventricular leads — 504

FIG. 5A

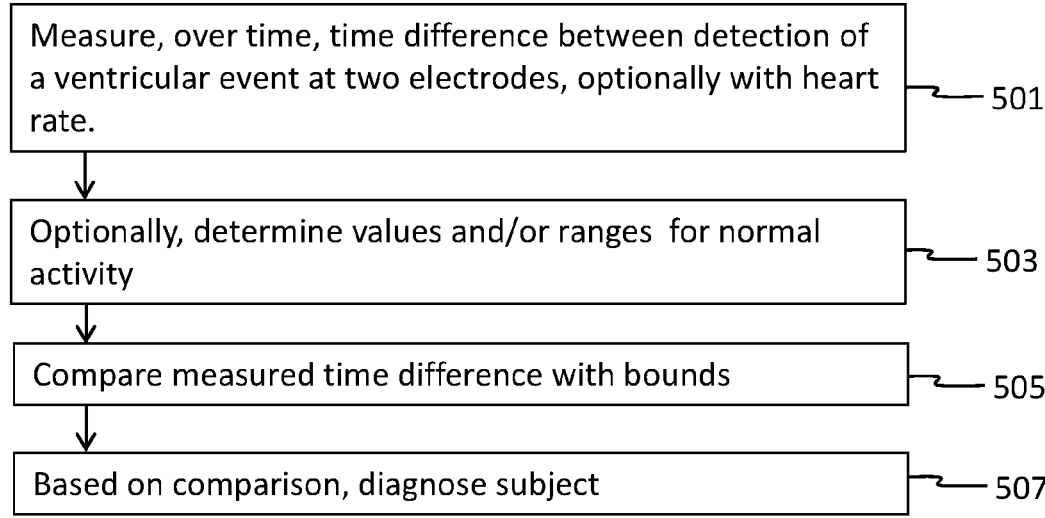

Measure, over time, time difference between detection of a ventricular event at two electrodes, optionally with heart rate. — 501

Optionally, determine values and/or ranges for normal activity — 503

Compare measured time difference with bounds — 505

Based on comparison, diagnose subject — 507

FIG. 5B

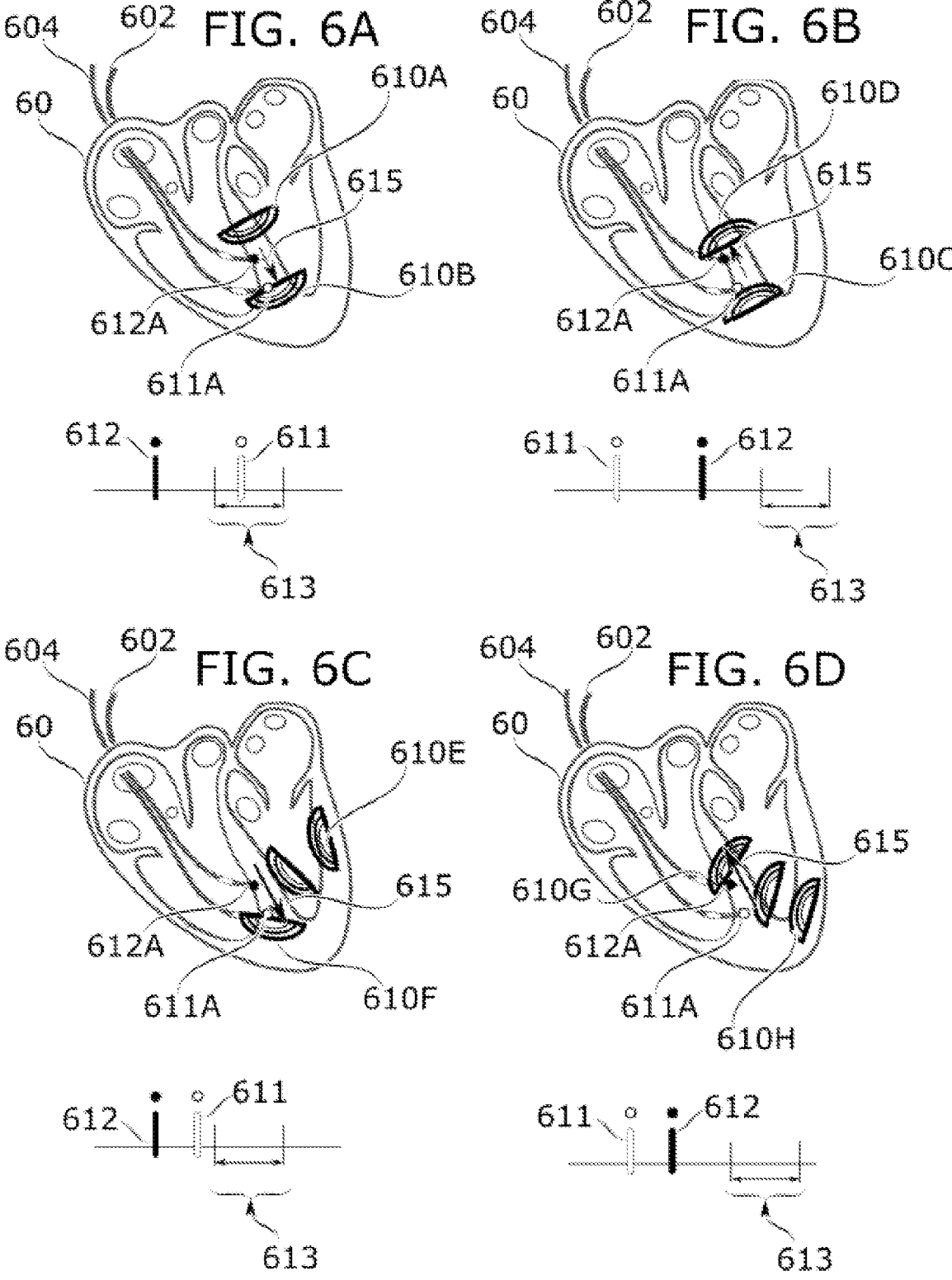

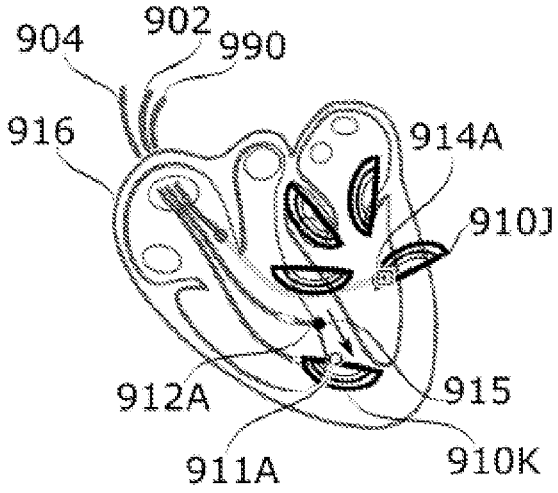
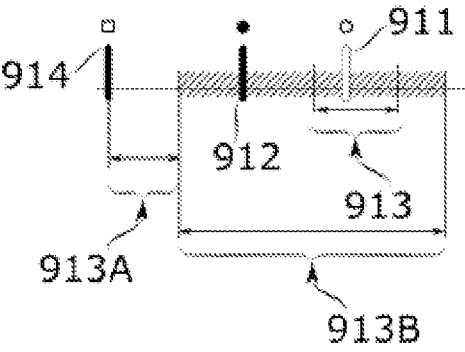
FIG. 9
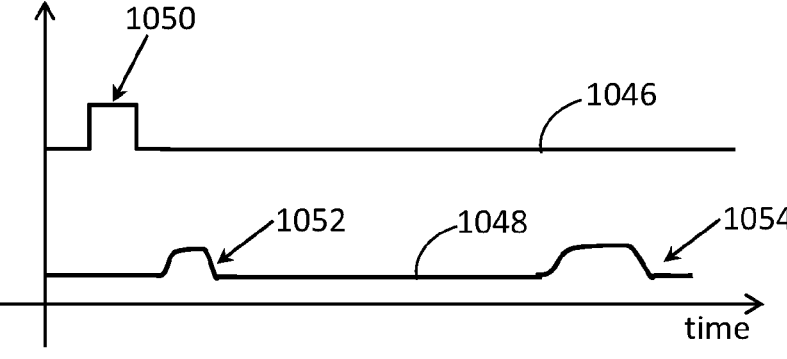
FIG. 10

LEAD POSITIONING FOR AN IMPLANTABLE PULSE GENERATOR

RELATED APPLICATIONS

This application is a National Phase of PCT Patent Application No. PCT/IB2022/052878 having International filing date of Mar. 29, 2022, which claims the benefit of priority under 35 USC § 119 (e) of U.S. Provisional Patent Application No. 63/167,192 filed on Mar. 29, 2021. The contents of the above applications are all incorporated by reference as if fully set forth herein in their entirety.

FIELD AND BACKGROUND OF THE INVENTION

The present invention, in some embodiments thereof, relates to a device for cardiac stimulation and, more particularly, but not exclusively, to a positioning of electrodes of a device for cardiac simulation.

Background art includes International Patent Application Publication No. WO2020/152619. The contents of this application is incorporated by reference as if fully set forth herein in its entirety.

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. A method of cardiac stimulation comprising:
receiving measurements from at least two electrodes positioned within the heart;
designating, from said measurements, a first electrode of said at least two electrodes and a second electrode of said at least two electrodes;
applying cardiac contractility modulation stimulation to said heart if a ventricular event is detected at said first electrode and then at said second electrode after a suitable time delay.
This and following methods may also be carried out using a controller suitably configured (e.g., using circuitry and/or software) to carry out these methods.

Example 2. The method according to example 1, wherein said designating comprises monitoring said measurements for a plurality of cardiac cycles and designating said first electrode for an electrode of said at least two electrodes which senses a ventricular event first for more than half of said cardiac cycles.

Example 3. The method according to any one of examples 1-2, wherein said measurements comprise cardiac electrical measurement signals from said at least two electrodes which are positioned at a right ventricle septum.

Example 4. The method according to any one of examples 1-3, wherein said designating comprises identifying, from said measurements, timing of arrival of a cardiac action potential wave-front at said at least two electrodes.

Example 5. The method according to any one of examples 1-3, comprising, wherein said at least two electrodes includes a first and a second electrode positioned at a septum and at least one additional electrode, where said measurements include measurement of potential at said first and said second electrode each with respect to said additional electrode.

Example 6. The method according to any one of examples 1-5, wherein said delay is at least 1 ms and at most 4 ms.

In any of the above examples, the method may include generating an alert if said delay is not within a desired range.

In any of the above examples, the method may include performing impedance measurements at and/or between said two electrodes.

In any of the above examples, the method may include performing said applying at both of said electrodes, overlapping in time.

In any of the above examples, the method may include performing said applying at both of said electrodes in a same cardiac cycle, at least in part, not overlapping in time.

Example 7. A method of monitoring comprising:
monitoring, over time, a time difference between arrival of a cardiac action potential wave-front at two electrodes, each positioned at a different point on a heart;
based on said monitoring one or more of:
designating relative position of the two electrodes, based on said time difference, for determination of which cardiac cycles should receive cardiac contractility modulation stimulation; and
optionally, but not necessarily, diagnosing a cardiac condition.

Example 8. The method according to example 7, wherein said two electrodes are each positioned at a different point on a heart septum.

Example 9. The method according to any one of examples 7-8, wherein said monitoring comprises, for a plurality of cardiac cycles:
receiving cardiac electrical measurement signals from said two electrodes;
identifying timing of arrival of a cardiac action potential wave-front at each of said two electrodes from said measurement signals;
determining a time difference between arrival of said cardiac action potential wave-front at said two electrodes, for a plurality of cardiac cycles; and
generating, from time differences determined for said plurality of cardiac cycles, a statistical representation of said time differences.

Example 10. The method according to example 7, wherein said determining comprises determining a sign of said time difference.

Example 11. The method according to example 9, wherein said wherein said statistical representation comprises a propensity of which electrode of said two electrodes senses said cardiac action potential wave-front first.

Example 12. The method according to any one of examples 7-11, wherein said designating comprises designating the electrode for which more than half of the wave-fronts are sensed first as being closer to an a trioventricular node.

Example 13. The method according to example 9, wherein said diagnosing comprises comparing said statistical representation with a threshold.

Example 14. The method according to any one of examples 9-13, comprising receiving heart rate measurements, for said plurality of cardiac cycles; and
wherein said generating comprises generating a statistical representation of said time differences with respect to heart rate.

Example 15. The method according to example 14, wherein if said statistical representation indicates increase in variation of time differences with increased heart rate, said diagnosing comprises diagnosing potential induced ischemia.

Example 16. The method according to example 15, wherein said increase heart rate includes statistical representations of said time differences for heart rates over a threshold rate.

Example 17. The method according to example 14, wherein if said statistical representation indicates increase in variation of time differences for one or more heart rate, said diagnosing comprises diagnosing potential cardiac arrhythmia.

Example 18. The method according to any one of examples 9-17, wherein said statistical representation of said time differences is a median of said time differences for a time period.

Example 19. The method according to example 18, wherein if said median deviates by more than a threshold value over a time period of less than a minute, lead dislodgement is identified.

Example 20. A method of cardiac signal processing of electrodes optionally previously positioned extending into the heart, comprising:

receiving measurements from at least two electrodes positioned within the heart;

determining, using said measurements, relative positioning of said at least two electrodes relative to each other;

evaluating suitability of said relative positioning of said at least two electrodes for measurement of cardiac activity to determine which cardiac cycles should receive cardiac contractility modulation stimulation.

Example 21. The method according to example 20, wherein said evaluating comprises generating a signal indicating whether one or more of said electrodes should be repositioned or anchored into position.

Example 22. The method according to example 20, wherein said measurements comprise cardiac electrical measurement signals from said at least two electrodes which are positioned at a right ventricle septum.

Example 23. The method according to any one of examples 20-22, wherein said determining comprises identifying timing of passage of a cardiac action potential wave-front from said measurement signals.

Example 24. The method according to example 23, wherein said wave-front is an intraseptal cardiac action potential wave-front.

Example 25. The method according to example 24, wherein said at least two electrodes comprises a first electrode and a second electrode; and wherein said determining comprises determining a delay between detection of said wave-front at said first electrode and detection of said wave-front at said second electrode.

Example 26. The method according to example 25, wherein said evaluating comprises evaluating said delay, wherein said delay is considered to indicate suitable positioning when said delay is at least 1 ms and at most 4 ms.

Example 27. The method according to any one of examples 20-26, wherein said evaluating comprises, for said relative positioning, determining a proportion of cardiac cycles which are eligible to receive cardiac contractility modulation stimulation.

Example 28. The method according to any one of examples 20-27, wherein said evaluating comprises evaluating a proportion of abnormal cardiac cycles which are determined to be eligible for cardiac contractility modulation stimulation.

Example 29. The method according to example 28, wherein said signal indicates that said electrodes should be repositioned if said proportion of abnormal cardiac cycles which are determined to be eligible for cardiac contractility modulation stimulation is more than 5% of the cardiac cycles.

Example 30. The method according to any one of examples 20-29, wherein said evaluating comprises evaluating a proportion of normal cardiac cycles which are determined not to be eligible for cardiac contractility modulation stimulation.

Example 31. The method according to example 30, wherein said signal indicates that said electrodes should be repositioned if said proportion of normal cardiac cycles which are not determined to be eligible for cardiac contractility modulation stimulation is more than 20% of the cardiac cycles.

Example 32. The method according to any one of examples 27-31, wherein said determining a proportion of cardiac cycles which are eligible to receive cardiac contractility modulation, is based on said measurements.

Example 33. The method according to any one of examples 20-32, wherein said at least two electrodes includes a first and a second electrode positioned at a septum and at least one additional electrode, where said measurements include measurement of potential at said first and said second electrode each with respect to said additional electrode.

Example 34. The method according to any one of examples 20-33, wherein said measurements are for a plurality of cardiac cycles.

Example 35. The method according to any one of examples 20-34, wherein said measurements includes measurements during which the heart is stimulated.

Example 36. The method according to any one of examples 20-35, comprising:

based on said evaluating, performing one or more of:

re-positioning one or more of said at least two electrodes; and anchoring said one or more of said at least two electrodes.

Example 37. The method according to example 36, wherein said receiving is performed a plurality of times to determine a plurality of delays; and wherein said evaluating comprises determining a statistical representation of said delay.

Example 38. The method according to example 37, wherein said statistical representation of said delay is a median of said plurality of delays.

Example 39. The method according to any one of examples 37-38, wherein said evaluating comprises comparing said statistical representation with a threshold.

Example 40. The method according to any one of examples 20-39, wherein said determining comprises determining a tissue impedance between said at least two electrodes.

Example 41. The method according to any one of examples 20-40, wherein said determining comprising injecting an electrical stimulation pulse;

wherein said measurements include electrical signals affected by said stimulation pulse; and wherein said determining comprises determining one or more parameter from said electrical signals affected by said stimulation pulse.

Example 42. The method according to example 41, wherein said injecting is during a refractory period of a cardiac cycle of said heart.

Example 43. The method according to any one of examples 41-42, wherein said injecting is between said at least two electrodes.

Example 44. A device for applying cardiac contractility modulation stimulation to a heart comprising:
  at least two electrodes; and
  circuitry configured to one or more of:
  determine relative positioning of said electrodes, using measurements collected with said electrodes; and
  based on said position, determine when to apply cardiac contractility modulation stimulation at said electrodes.

Example 45. The device according to example 44, comprising:
  a first lead; and
  a second lead;
  wherein said at least two electrodes comprise four electrodes comprising:
  a first electrode and a second electrode hosted by said first lead;
  a third electrode and a fourth electrode hosted by said second lead.

Example 46. The device according to example 45, wherein said first and third electrodes are configured to be attached a septum of the heart.

Example 47. A system for cardiac stimulation comprising:
  a device according to example 44;
  circuitry configured to evaluate a suitability of said relative positioning of said at least two electrodes for measurement of cardiac activity to determine which cardiac cycles should receive cardiac contractility modulation stimulation;
  a user interface connected to said circuitry configured to transmit said suitability to a user.

Example 48. A method of cardiac signal processing comprising:
  receiving measurements from at least two electrodes optionally previously positioned within the heart;
  determining, using said measurements, position of said at least two electrodes within said heart;
  evaluating suitability of said positioning of said at least two electrodes for measurement of cardiac activity to determine which cardiac cycles should receive cardiac contractility modulation stimulation.

Example 49. The method according to example 48, wherein said determining comprises identifying timing of passage of a cardiac action potential wave-front from said measurement signals.

Example 50. The method according to example 49, wherein said determining comprises determining a delay between detection of said cardiac action potential wave-front between a first electrode of said at least two electrodes and a second electrode of said at least two electrodes.

Example 51. The method according to example 50, wherein said evaluating comprises evaluating said delay.

Example 52. A method of monitoring comprising:
  monitoring, over time, a time difference between arrival of a cardiac action potential wave-front at two electrodes, each positioned at a different point on a heart;
  identifying electrode dislodgement, based on said monitoring.

Example 53. A method of cardiac signal processing, which is optionally carried out using a system with circuitry (optionally implantable) and at least two electrodes in the heart, and configured for carrying out the method, comprising:
  injecting an electrical stimulation pulse at a first electrode positioned within a heart;
  receiving measurements of electrical signals affected by said stimulation pulse, from a second electrode positioned within the heart;

determining, using said measurements, relative positioning of said first and said second electrode.

Example 54. The method of cardiac signal processing according to example 53, comprising:
  evaluating suitability of said relative positioning of said first electrode and said second electrode for measurement of cardiac activity to determine which cardiac cycles should receive cardiac contractility modulation stimulation.

Example 55. The method according to example 54, wherein said measurements comprises a measurement pulse; and wherein said determining comprises determining a change in amplitude between said injected pulse and said measured pulse.

Example 56. The method according to any one of examples 53-55, wherein said injecting is during a refractory period of a cardiac cycle.

Example 57. The method according to any one of examples 53-54, wherein said injecting is during a different part of a cardiac cycle than a refractory period.

Example 58. The method according to example 57, wherein said determining comprises determining a delay between injecting said pulse and measuring said pulse.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof.

Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting cardiac measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL
VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5A is a method of electrode selection for implementing methods of controlling an implantable pulse generator, according to some embodiments of the invention;

FIG. 5B is a method of monitoring, according to some embodiments of the invention;

Figures 7A, 7B, 7C, 7D, 7E:
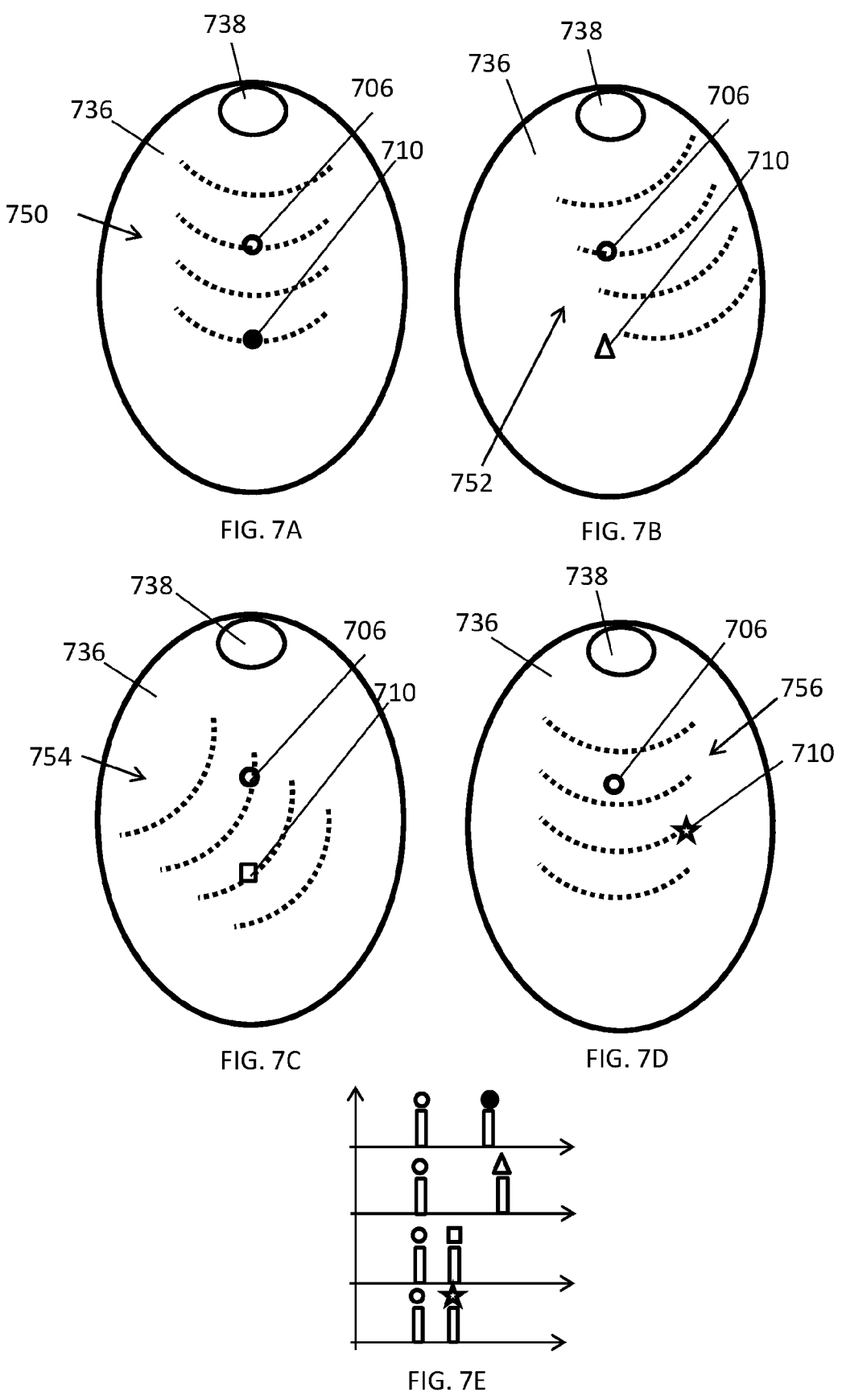
Figures 8A, 8B, 8C, 8D, 8E:
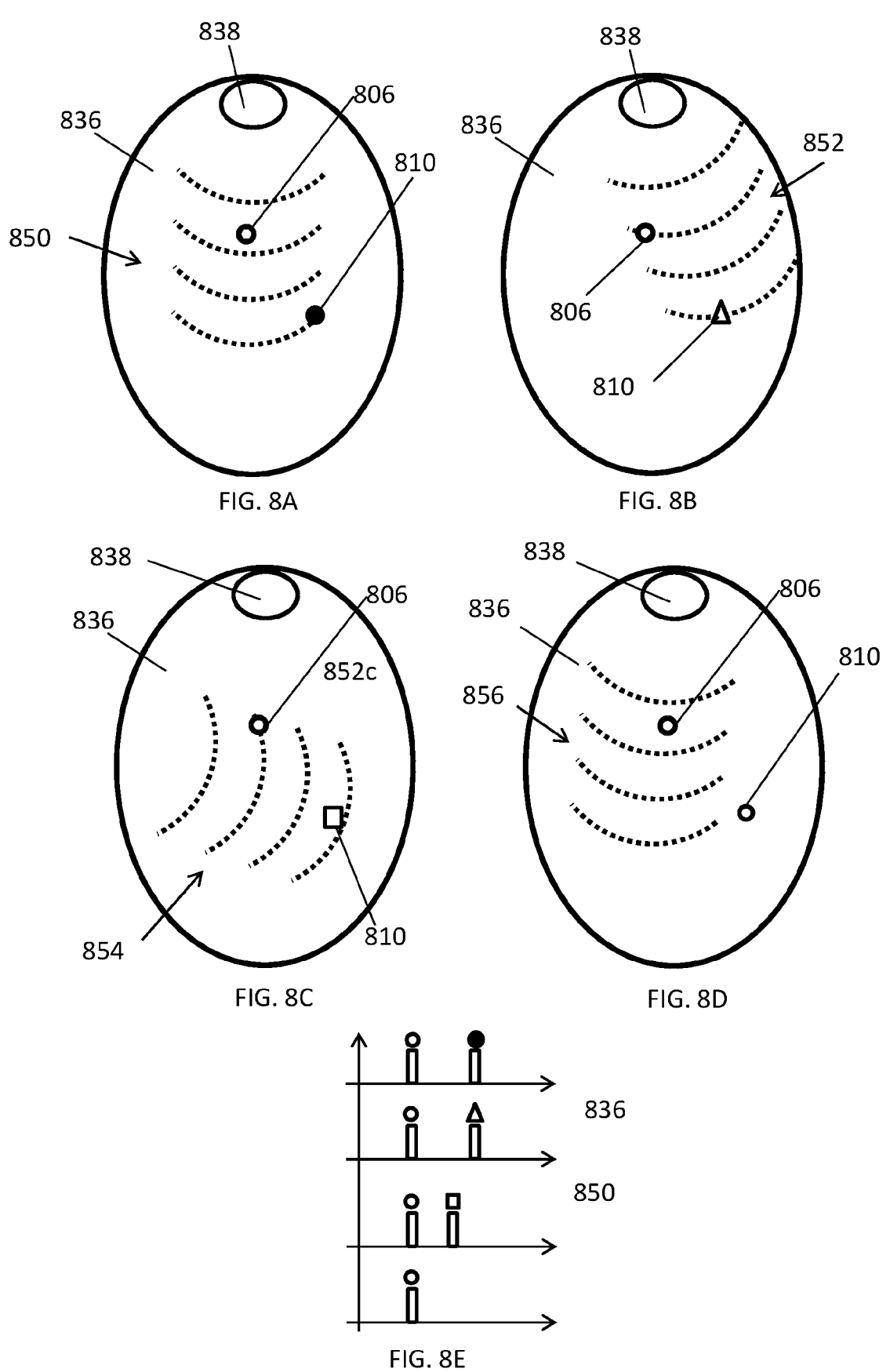

FIGS. 6A-D are schematic illustrations of discrimination of conduction patterns passing through a ventricular septum 636, according to some embodiments of the invention;

FIGS. 7A-D are simplified schematic illustrations of sensing of cardiac conduction wave-fronts, according to some embodiments of the invention;

FIG. 7E is a simplified schematic illustration of timelines of sensed ventricular events, according to some embodiments of the invention;

FIGS. 8A-D are simplified schematic illustrations of sensing of cardiac conduction wave-fronts, according to some embodiments of the invention;

FIG. 8E is a simplified schematic illustration of timing of a sensed ventricular events, according to some embodiments of the invention;

FIG. 9 is a schematic illustration of three-sensor discrimination of conduction patterns passing through a ventricular septum, according to some embodiments of the invention; and FIG. 10 is a simplified schematic showing a stimulation signal and a measurement signal, according to some embodiments of the invention.

DESCRIPTION OF SPECIFIC EMBODIMENTS OF THE INVENTION

The present invention, in some embodiments thereof, relates to a device for cardiac stimulation and, more particularly, but not exclusively, to a positioning of electrodes of a device for cardiac simulation.

Overview

A broad aspect of some embodiments of the invention relates to determining positioning of electrodes for sensing of cardiac electrical activity within a heart, using measurements collected using the electrodes themselves.

In some embodiments, sensing of cardiac electrical activity with the electrodes is used to determine which cardiac cycles, (e.g. on a per cycle basis) receive cardiac contractility modulation (cardiac contractility modulation) stimulation. Where, in some embodiments, cardiac contractility modulation is applied to the septum, for example, between two electrodes positioned (e.g. anchored) at the septum. Additionally and optionally, in some embodiments, sensing of cardiac electrical activity with the electrodes is used to determine when implantable cardioverter-defibrillator (ICD) simulation and/or cardiac resynchronization therapy (CRT) stimulation is applied.

In some embodiments, assumed and/or determined electrical cardiac signal propagation for normal (e.g. non-arrhythmic) cardiac cycles is used along with measurements of cardiac electrical activity collected with the electrodes to determine position of the electrodes.

Where, in some embodiments, measurement of cardiac electrical activity includes relative timing of arrival of a cardiac conduction wave-front between a first measurement position and a second measurement position.

Where, in some embodiments, measurement at the first measurement position is collected using an first electrode pair where a first electrode of the first electrode pair is positioned at the first measurement position and a second electrode of the first electrode pair is positioned at a distance from the first electrode. Where, in some embodiments, measurement at the second measurement position is collected using a second electrode pair where a first electrode of the second electrode pair is positioned at the second measurement position and a second electrode of the second electrode pair is positioned at a distance from the first electrode of the second electrode pair.

In some embodiments, the first electrodes of both pairs of electrodes are in contact with a heart septum for example, connected (e.g. anchored) to the septum. In some embodiments, the first electrodes of both pairs are each hosted by a different cardiac lead. In some embodiments, the second electrodes are hosted by one or more of the leads, at a distance from the first electrodes, the second electrodes, for example, being positioned within a heart chamber e.g. the right ventricle (RV).

In some embodiments, there is a single second electrode, with, for example, both measurement at the first electrode of the first pair and measurement at the first electrode of the second pair being with respect to the single second electrode. In some embodiments, each lead hosts a second electrode, where, in some embodiments, measurement at each respective first electrode being with respect to the second electrode hosted by the same lead as the first electrode.

In some embodiments, cardiac contractility modulation stimulation is applied to a heart when a cardiac conduction wave-front is detected at a first electrode and then at a second electrode. In some embodiments, the stimulation is applied when there is a sufficient delay between detection at the first and second electrode.

An aspect of some embodiments of the invention relates to, once the two electrodes are positioned within a heart, designating which electrode is considered to be a first electrode and which electrode is considered to be a second electrode using measurements collected at the electrodes themselves. For example, in some embodiments, once positioned, the first electrode to detect a cardiac conduction wave-front is designated to be the first electrode, and only those cardiac cycles for which the cardiac conduction wave-front is detected at the second electrode after the first electrode (e.g. with a suitable time delay) receive cardiac contractility modulation stimulation.

In some embodiments, the electrodes are given designations based on statistical analysis of which electrode senses the cardiac conduction wave-front first. For example, in some embodiments, for a given time period, the electrode which detects the cardiac conduction wave-front first for more than half of the cardiac cycles in the given time period is designated to be the first electrode.

In some embodiments, feature/s of electrical cardiac signal propagation for normal cardiac cycles is determined using the electrodes. Where, in some embodiments, a plurality of measurements are used to provide a statistical understanding of what constitutes normal propagation and/or an expected prevalence of normal cardiac cycles.

In some embodiments, a single set of measurements collected with the electrodes is used to both determine position of the electrodes and feature/s of cardiac cycle/s for the subject.

In some embodiments, electrode and/or lead position is determined by electrical stimulation provided at an electrode (and/or between an electrode pair) while, at another electrode (and/or between another electrode pair) the effect/s of the stimulation are sensed. Optionally, in some embodiments, the same electrodes used to sense cardiac conduction wave-fronts are used in impedance measurement/s.

For example, in some embodiments, distance between electrodes is determined from tissue impedance measurement/s where tissue impedance is, in some embodiments, measured between electrodes (e.g. between two electrodes) proximal to and/or coupled to and/or anchored to and/or embedded in heart tissue.

In some embodiments, stimulation and measurement is using a single pair of electrodes, where simulation is injected at one of the electrodes and measured at the other. In some embodiments, tissue impedance measurements are collected using two pairs of electrodes, where electrical stimulation is supplied between a first pair of electrodes and measurement is between a second pair of electrodes. In some embodiments, a measurement pair of electrodes is formed by electrodes proximal to (e.g. attached to e.g. anchored to) heart tissue e.g. septal tissue. In some embodiments, the measurement pair of electrodes is hosted by two leads, each lead hosting a measurement electrode e.g. at the lead tip.

In some embodiments, impedance measurements are collected by injecting an electrical stimulation pulse between electrodes of a stimulation electrode pair and measuring amplitude decrease of the pulse.

In some embodiments, distance between electrodes is determined by measuring an action potential travel time between the electrodes, e.g. by stimulating cardiac tissue and then measuring the time for electrical activity associated with consequent ventricle contractility to be detected at one or more other electrodes. Optionally, in some embodiments, the same electrodes used to sense cardiac conduction wave-fronts and/or impedance are used in action potential measurement/s.

For example, in some embodiments, stimulation is provided between a stimulation electrode pair and action potential is measured between a measurement electrode pair. Where, in some embodiments, each electrode of the measurement electrode pair is connected to a different region of septum.

In some embodiments, tissue impedance and action potential travel speed measurements are collected using the same applied stimulation (e.g. stimulation pulse). For example, exploiting potential faster speed of tissue conduction than cell to cell activation travel of action potential of cardiac tissue. For example, in some embodiments, after a stimulation pulse, a first pulse detected at a measurement electrode pair is used for determining tissue impedance and a second pulse detected is used to indicate action potential travel time. An aspect of some embodiments of the invention relates to positioning electrodes for sensing of cardiac electrical activity within a heart, for example, when installing a cardiac stimulation device, using position feedback determined from electrode measurements. In some embodiments, positioning of electrodes is by positioning lead/s hosting the electrodes.

In some embodiments, electrode leads are introduced into the heart, position of the electrodes are determined using electrode measurements and the determined position is then evaluated, evaluation indicating that the leads should be repositioned and/or that their position should be maintained e.g. by anchoring.

In some embodiments, measurement feedback is used to position electrode leads so that cardiac electrical measurements collected using the leads produce a minimal number of indications that cardiac contractility modulation stimulation should be suppressed e.g. where indication is of cardiac cycle abnormality and/or failure to detect arrival of a cardiac conduction wave-front at one or more electrode.

For example, in an exemplary embodiment, positions for a first and second electrode are selected to provide sensing of a cardiac conduction wave-front at both electrodes and where one of the two electrodes senses the wave-front prior to the other and with a sufficient delay between the sensing of the wave-front.

In some embodiments, positioning of the electrodes e.g. during installation of the leads is an iterative process where electrodes are positioned, and/or measurements taken repetitively e.g. until a desired position is reached. Where, in some embodiments, the desired position is defined by timing of sensing of cardiac wave-fronts and/or incidence of indications that cardiac contractility modulation stimulation should be suppressed.

In some embodiments, electrodes are positioned and repositioned until a position of maximum delay is located. In some embodiments, electrodes are repositioned until the delay is above a threshold duration (and/or within an allowed range).

An aspect of some embodiments of the invention relates to monitoring positioning of electrode leads and/or cardiac health using measurement's collected with the leads.

In some embodiments, cardiac cycle measurements are monitored e.g. for changes e.g. over time. In some embodiments, the change/s are then evaluated to provide an indication of change in cardiac behavior and/or change in lead positioning (e.g. dislodgement). In some embodiments, evaluation includes collecting additional measurements.

In some embodiments, relative timing between (e.g. a delay between) detected cardiac wave-front arrival at different electrode positions is monitored. Where, in some embodiments, the delay is monitored, with heart rate.

In some embodiments, one or more statistical representation (e.g. average) of the delay is monitored. Where, in some embodiments, In some embodiments, if the delay, and/or a statistical representation of the delay is outside a normal range, lead dislodgement and/or a cardiac condition is diagnosed. In some embodiments, the normal range is tailored to the particular patient, for example, potentially enabling tracking of a change in cardiac behavior and/or health for example, in the case of a subject with existing cardiac malfunction/s.

In some embodiments, a median delay between detected cardiac wave-fronts is monitored. In some embodiments, change in the median delay, for example, outside a threshold and/or allowed range, is used to diagnose a change in cardiac health of the subject. Potentially, a median delay is used to demonstrate a change in cardiac behavior. For example, as, even in subjects suffering from arrhythmia, expected arrhythmic cycles have an incidence of less than 20%.

In some embodiments, rapidity of change of the time delay (and/or statistical representation of the time delay) is monitored. For example, where, a rapid change in time delay and/or statistical representation of the time delay (e.g. average time delay) in some embodiments is used to identify lead dislodgement. Whereas, in some embodiments, a more gradual change is used to predict change in cardiac behavior.

In some embodiments, the delay itself is used to identify lead dislodgement and/or diagnose cardiac behavior optionally, where the delay (and/or statistical representation of the delay) is evaluated with heart rate (e.g. average delay for different ranges or heart rate). Alternatively or additionally, in some embodiments, how much the delay varies is used to identify lead dislodgement and/or diagnose cardiac behavior.

In some embodiments, induced ischemia is associated with an increase in variation in the delay between detected cardiac wave-fronts, when heart rate is increased e.g. above a threshold.

In an exemplary embodiment, if a statistical representation of the time difference between detected cardiac conduction wave-fronts (e.g. a median time difference) increases (e.g. above a threshold) with heartrate, potential induced ischemia is diagnosed.

An aspect of some embodiments of the invention relates to determining distance between electrodes positioned within a heart e.g. relative distance between electrodes by injection of a stimulation pulse between the electrodes. In some embodiments, the electrodes are positioned at (e.g. anchored to) a septum of the heart. In some embodiments, the stimulation pulse is applied at a first electrode and is measured at a second electrode. In some embodiments, the pulse is applied during a refractory period of a cardiac cycle of the heart for example to generate a measurement pulse (e.g. at the second electrode) where a reduction in amplitude is used to determine distance between the electrodes. Alternatively or additionally, the stimulation pulse is applied not during the refractory period of the cardiac cycle to stimulation a second measurement pulse of stimulation cardiac action potential in the tissue between the electrodes the measurement of which (e.g. delay between stimulation and detection of the measurement pulse) in some embodiments, is used to determine distance between and/or relative positioning of the electrodes (e.g. simulation and measurement electrodes).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary System

Figures 1, 2:
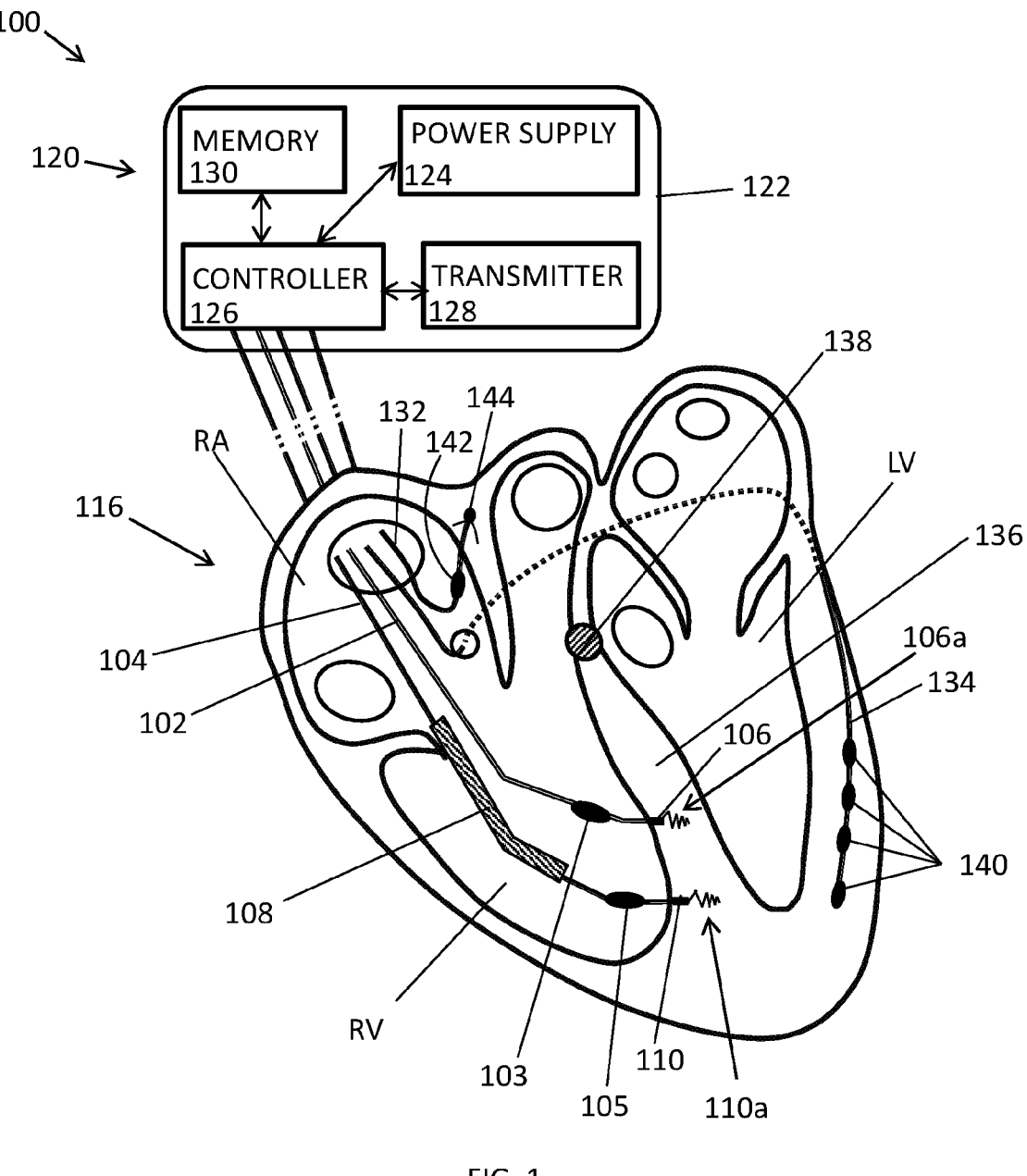
FIG. 1 is a simplified schematic of a system for cardiac stimulation, according to some embodiments of the invention.
FIG. 2 is a method of evaluating electrode position, according to some embodiments of the invention.

FIG. 1 is a simplified schematic of a system 100 for cardiac stimulation, according to some embodiments of the invention.

In some embodiments, system 100 is a system for applying contractility modulation. Additionally or alternatively, in some embodiments, system 100 is configured to apply other type/s of cardiac stimulation e.g. pacing.

In some embodiments, system 100 is configured to collect cardiac conduction wave-front measurements from at least two points within a heart 116, for example, within a right ventricle RV of heart 116. In an exemplary embodiment, measurement of cardiac wave-fronts passing through a septum 136 are collected.

In some embodiments, measurements are collected using at least two electrodes. In an exemplary embodiment, bipolar measurements are collected using at least two electrode sets. Where, for example, for each set, measurement is between a first electrode and a second electrode. In some embodiments, each set has an individual first electrode 103, 105 and an individual second electrode 106, 110 respectively. Where, in an exemplary embodiment, a first lead 102 hosts a first electrode 103 and a second electrode 106 of a first electrode set and a second lead 104 hosts a first electrode 105 and a second electrode 110 of a second electrode set. Alternatively, in some embodiments, there are fewer second electrodes than first electrodes. In some embodiments, "bipolar electrodes" are used to collect measurements where a bipolar electrode includes a first and a second electrode, for example, as described elsewhere in this text. For example, on a single lead e.g. where one electrode (e.g. the "first electrode') is in contact with tissue to be measured and the other electrode (e.g. the "second electrode") is at a distance from the tissue to be measured.

In an exemplary embodiment, electrodes 103, 105 are ring electrodes.

In an exemplary embodiment one or more electrode set includes a first electrode 106, 110 in contact with and/or in close proximity to septum 136 and a second electrode 103, 105 of the set is at a distance from the first electrode e.g. located within the right ventricle. In some embodiments, one or both of leads 102, 104 extend into the right ventricle through the same blood vessel (e.g., the superior vena cava). In some embodiments, first electrodes 106, 110 of one or more set are located at tip portions of first lead 102 and second lead 104. In some embodiments, second electrodes 103, 105 of one or more set are hosted in a body portion of leads 102, 104 respectively.

Figure 4:
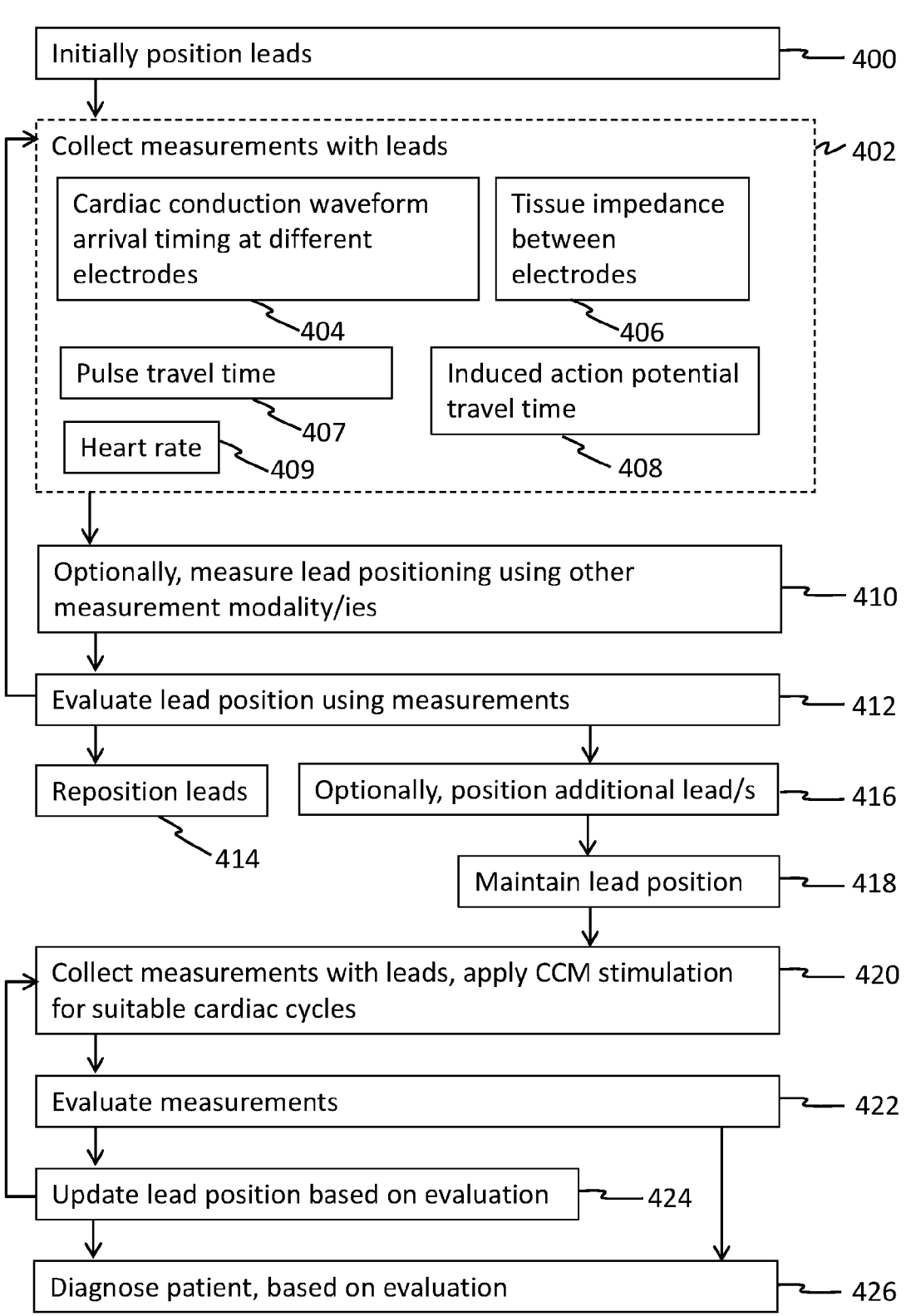
FIG. 4 is a method of applying cardiac contractility modulation stimulation, according to some embodiments of the invention.

Optionally, in some embodiments, one or more of electrodes 103, 105, 106, 110 are configured to deliver electrical energy to the heart (e.g. for measuring distance between the electrodes e.g. including one or more feature as illustrated in and/or as described regarding one or more of steps 406, 407, 408 of FIG. 4).

In some embodiments, one or both of right ventricle leads 102, 104 include anchors 106a, 110a respectively. Where, in some embodiments, anchors 106, 110 are designed to hold leads 102, 104 to heart tissue and position electrodes 103, 105 within RV. Anchors 106a, 110a, for example, configured to anchor leads 102, 104 to septum 136 of heart 116. In some embodiments, distal ends of one or more of leads 102, 104 and/or anchors 105, 110 include conductive material. The conductive material, in some embodiments, used as measurement electrodes 106, 110 (e.g. as described regarding step 412 FIG. 4).

In some embodiments, therapeutic current delivery (e.g. cardiac contractility modulation) is applied at one or more electrodes within the heart. For example, at one or more electrodes 106, 110 (e.g. between the electrodes) positioned (e.g. anchored) at septum 136. It is noted that therapeutic current delivery is optionally provided during a relative and/or an absolute refractory period. Optionally or additionally, this current is configured to cause remodeling of the heart, for example, by modifying and/or reversing a fetal gene program of a heart with heart failure. Such a therapeutic signal may be applied, for example, using an "Optimizer® Smart" implantable device sold by Impulse Dynamics, Inc. of Marlton NJ, USA.

In some embodiments, therapeutic current delivery (e.g. cardiac contractility modulation) is applied at one or more leads within the heart. For example, at one or more leads 102, 104 through one or more bipolar electrodes set, for example the set including electrode 103 and electrode 106 and/or the set including electrode 105 and electrode 110.

Alternatively or additionally, in some embodiments, system 100 includes one or more element 108 for therapeutic current delivery (e.g. implantable cardioverter-defibrillator (ICD) simulation and/or cardiac resynchronization therapy (CRT) stimulation) to heart 116 e.g. a shock coil 108. In an exemplary embodiment, shock coil 108 is hosted by second lead 104. In some embodiments, shock coil 108 is positioned on second lead 104 such that, when second electrode 105 is positioned in a desired position and/or when second lead 104 is anchored to septum 136, shock coil 108 is located at least partially within RV. In some embodiments, shock coil 108 is sufficiently long that, in some embodiments, shock coil 108 extends into the right atrium (RA) e.g. as illustrated in FIG. 1.

Optionally, in some embodiments, system includes one or more additional electrode for measurement of cardiac electrical activity and/or delivery of electrical stimulation. For example, one or more atrial electrode 142, 144 and/or one or more left ventricle wall electrode 140. In some embodiments, system 100 includes one or more additional lead 132, 134. For example, in some embodiments, system 100 includes a right atrium (RA) lead 132 which, in some embodiments, hosts one or more atrial electrode 142, 144.

For example, in some embodiments, system 100 includes a left ventricle (LV) lead 134, which, in some embodiments, hosts one or more electrode 140. In some embodiments, LV lead 134 extends into a blood vessel of the LV e.g. a vein. In some embodiments, lead 134 includes a plurality of electrodes disposed along the lead e.g. four electrodes. In some embodiments, lead 134 hosts at least two electrodes 140. In an exemplary embodiment, lead 134 hosts four electrodes 140. In some embodiments, electrical stimulation is provided between one or more electrode pairs of electrodes 140. Where, for example, stimulation is one or more of ICD and/or CRT.

In some embodiments, system 100 includes an implantable pulse generator (IPG) 120. In some embodiments, IPG 120 includes a housing 122 which is configured for implantation e.g. sized and/or shaped to be implanted subcutaneously and/or including biocompatible material e.g. a biocompatible coating.

In some embodiments, IPG 120 includes a controller 126 configured to generate and/or send control signals.

Optionally, in some embodiments, IPG includes a transmitter 128 which is, for example configured to send collected messages to a receiver. For example a receiver external to the patient's body. In some embodiments, the external receiver is connected to a user interface, for issuing of alert/s to user/s (the patient themselves and/or healthcare professional/s). In some embodiments, transmitter 128 includes a receiver, for example, configured to receive control instructions e.g. for controller 126 e.g. for change in operation of IPG.

In some embodiments, IPG 120 includes a power supply 124 which is configured to provide power to one or more part of system 100. For example, to one or more of shock coil 108, controller 126, transmitter 128 and memory 130. For example, in some embodiments, power supply 124 provides shock coil 108 with electrical power. In some embodiments, controller 126 receives measurement data from one or more sensor (e.g. lead electrodes 103, 105, 106, 110, 142, 144, 140).

Exemplary Method of Evaluating Electrode Position

FIG. 2 is a method of evaluating electrode position, according to some embodiments of the invention.

At 200, in some embodiments, cardiac electrical activity of the heart is measured. For example, using one or more electrode positioned within the heart. In an exemplary embodiment, passage of cardiac conduction wave-fronts passing through a septum are measured using at least two electrode sets e.g. electrode set 103, 106 and electrode set 105, 110 FIG. 1.

At 202, in some embodiments, measurements collected in step 200 are used to evaluate position of one or more electrode positioned within the heart. Where, in some embodiments, evaluating includes one or more feature as illustrated in and/or described regarding step 412 and/or step 422 of FIG. 4.

Exemplary Method of Cardiac Contractility Modulation Stimulation

Figure 3A:
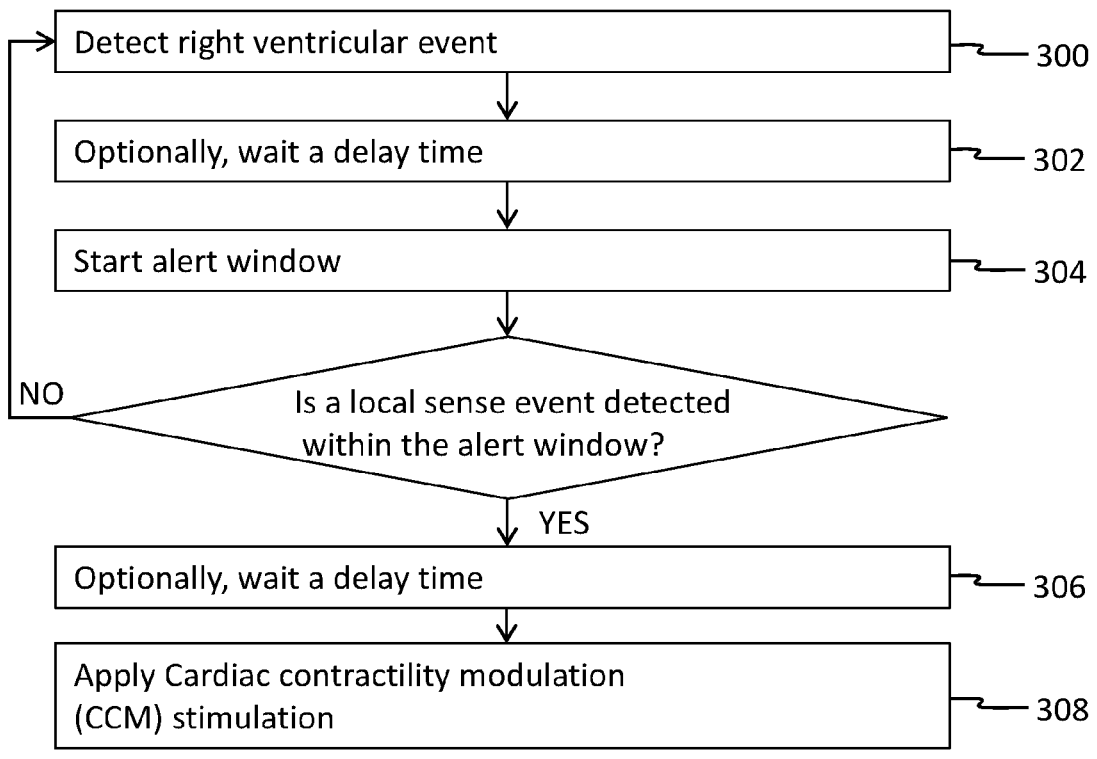
FIG. 3A is a method of controlling an implantable pulse generator, according to some embodiments of the invention.

FIG. 3A is a method of controlling an implantable pulse generator, according to some embodiments of the invention.

At 300, in some embodiments, arrival of a cardiac electrical activity wave-front (also termed "cardiac conduction wave-front" and herein also termed "ventricular event") is determined from measurements collected by an electrode pair designated as being a RV electrode pair. In some embodiments, the ventricular event is a timing of arrival of an R-wave component of a heart electrocardiogram (ECG). The R-wave component has potential advantages for this use insofar as it is relatively large in amplitude and relatively fast; however, any other component of the ongoing cycling heart electrical activity waveform is detected additionally or alternatively to the R-wave. In some embodiments, timing of the ventricular event is determined by identifying a peak of the R-wave. Alternatively or additionally or template correlation is used to identify the R-wave.

At 302, optionally, in some embodiments, a delay time (e.g. delay 302 FIG. 3B) is introduced after the ventricular event is detected.

In some embodiments, the delay time is between about 0-100 msec or between about 0-50 msec, or lower or higher or intermediate durations or ranges.

At 304, in some embodiments, a discrimination window (e.g. discrimination window 304 FIG. 3B) is started.

In some embodiments, the discrimination window closes about 1-75 msec after it begins, or about 1-40 msec after it begins, or lower or higher or intermediate ranges or durations. At 306, in some embodiments, if, during the discrimination window, a ventricular event is detected at an LS designated electrode set (also herein termed a "local sense (LS) event"), optionally, a delay time (e.g. delay 306 FIG. 3B) is introduced. The delay time, for example, being implemented upon detection of the LS event.

At 308, in some embodiments, directly after detection of the LS event (or, in the case of a delay time at step 306, after the delay time) cardiac contractility modulation is applied. In some embodiments, if a LS event is not detected within the discrimination window, cardiac contractility modulation is not applied e.g. during that cardiac cycle. Additionally or alternatively, in some embodiments, if a LS event is not detected within the discrimination window, cardiac contractility modulation is not applied during one or more subsequent cardiac cycles.

In some embodiments, duration of one or more of; delay time 302, discrimination window 304, delay time 306, and cardiac contractility modulation stimulation duration 308 are adjustable and/or variable. For example, one or more of the durations being dependent on heart rate. For example, in some embodiments, one or more of the durations is determined as a percentage of the heart rate. For example, where heart rate is determined from heart rate measurements for a time duration and/or number of cycles. For example, 2-100 cycles, or 2-50 cycles, or 1-30 seconds, or lower or higher or intermediate numbers of cardiac cycles or durations. In some embodiments, heart rate is continuously adjusted with recent data. In some embodiments, heart rate is determined periodically from recent data, where the value determined is used until a new value is determined.

In some embodiments, cardiac contractility modulation is performed when heart rhythm frequency is above a minimum threshold and/or below a maximum threshold e.g. within an allowed range.

For example, in some embodiments, cardiac contractility modulation is provided during exercise. For example, for heart rates of up to an upper threshold. Where, in some embodiments, the upper threshold for an individual is a maximal exercise rate (in beats per minute, BBM). Where, in some embodiments, the maximal exercise rate, M, for an individual where A is an age of the individual, is determined as: M=220−A In some embodiments, the upper threshold for an individual is 60%, or 70%, or 80%, or 85%, or 90%, or 95%, or lower or higher or intermediate ranges or percentages of the maximal exercise rate.

In some embodiments, cardiac contractility modulation is provided for heart rates of above a lower threshold. Where, in some embodiments, the lower threshold is about 100 BPM, or about 110 BPM, or about 120 BPM or lower or higher or intermediate rates or ranges.

For example, an allowed rage for cardiac contractility modulation is between a lower threshold and an upper threshold e.g. as delineated above.

The windowing algorithm is explained herein for purposes of illustration. It has the potential advantage of being calculable with a minimum of computational resources, and/or implemented by analog timing circuitry. The same cardiac electrical stimulation (e.g. cardiac contractility modulation stimulation) and/or suppression of stimulation outcomes, in some embodiments, are obtained in another fashion. For example, in some embodiments, apparent speed and direction of a cardiac conduction vector (e.g. 615 FIGS. 6A-D) are explicitly determined, and a conduction vector which falls within a certain parameter range for its speed and/or direction is used to determine if to apply cardiac contractility modulation.

Figure 3B:
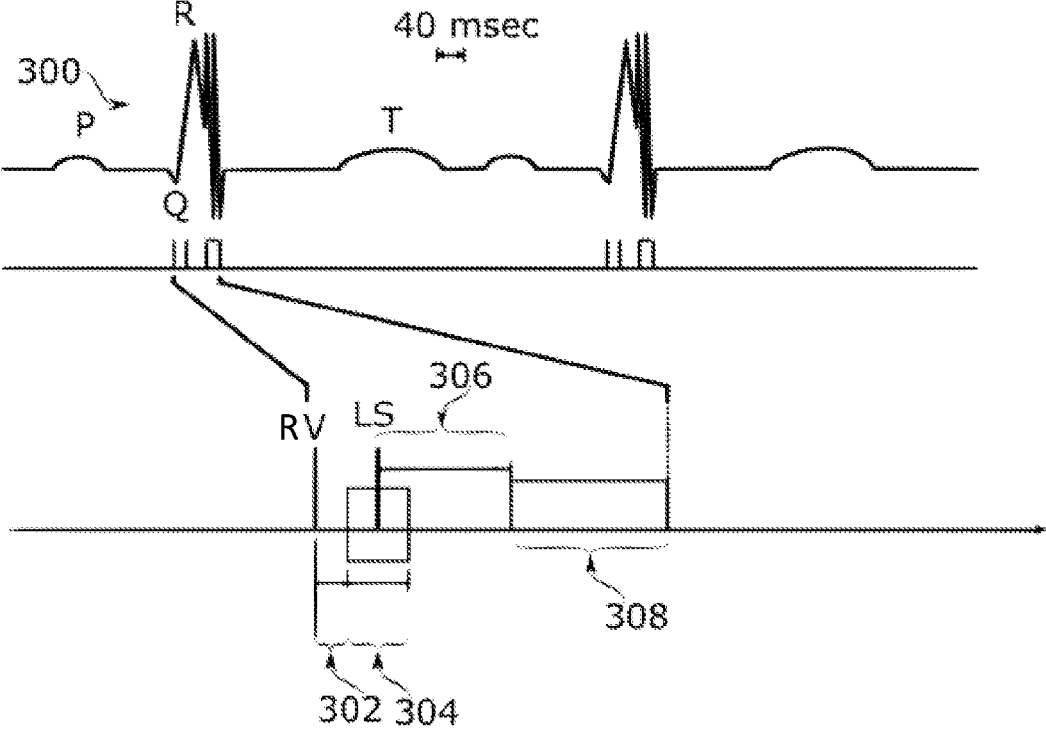
FIG. 3B is a schematic representation of operation of a method of controlling an implantable pulse generator, according to some embodiments of the invention.

FIG. 3B is a schematic representation of operation of a method of controlling an implantable pulse generator, according to some embodiments of the invention.

Illustrated in FIG. 3B is a cardiac cycle trace 300 showing P, Q, R and T portions of the cardiac cycle.

In some embodiments, a right ventricular event (also termed RV event) is detected, for example, upon transition between Q and R portions of the cardiac cycle. Where, in some embodiments, RV event detection is from electrical signals measured by an electrode designated as being a RV electrode (e.g. first electrode 103 FIG. 1). Delay 302 is then introduced before a start of a discrimination window 304. If a local sense LS event is detected (e.g. from electrical signals measured by second electrode 105 FIG. 1) during discrimination window 304, optimally, in some embodiments, a delay 306 (termed "second delay" and delay 302 termed "first delay" if delay 302 has been enacted) is introduced upon the LS event detection after which, in some embodiments, cardiac contractility modulation stimulation 308 is applied.

Exemplary Detailed Method of Cardiac Contractility Modulation Stimulation

FIG. 4 is a method of applying cardiac contractility modulation stimulation, according to some embodiments of the invention.

At 400, in some embodiments, one or more electrode (e.g. hosted by one or more lead) of a cardiac device are positioned at initial positions within a heart.

In some embodiments, one or more lead and, in an exemplary embodiment, a plurality of leads are delivered to inner chamber/s of a heart. Where one or more lead hosts one or more electrode. Where each electrode is configured to sense electrical activity of the heart and/or is configured to deliver cardiac contractility modulation.

In an exemplary embodiment, at least a first electrode and a second electrode are configured to detect passage of electrical cardiac wave-fronts passing through a septum of the heart. In some embodiments, the first and second electrodes detect the wave-fronts when positioned in proximity to the septum. For example, as described elsewhere in this document, timing of arrival of a cardiac wave-front (e.g. through the septum) and, in particular, delay between detection of the cardiac wave-front between the first and the second electrode (herein termed "delay") is identified from measurement signals of the first and second electrodes.

In some embodiments, lead delivery is through a catheterization procedure, optionally assisted by imaging e.g. one or more of ultrasound, x-ray (e.g. fluoroscopy). In some embodiments, lead/s are advanced into the heart using a catheterization process where, in some embodiments, pressure is applied to a distal portion of the lead to advance a proximal portion of the lead into the heart and/or tension is applied to the distal portion of the lead to retract the proximal portion from the heart.

In some embodiments, (e.g. prior to positioning the lead/s) position for one or more lead portion is selected.

For example, in some embodiments, a medical practitioner selects lead portion positioning, for example, as the medial practitioner prepares to implant a cardiac stimulation system and/or position and/or re-position portion/s of an implanted system (e.g. the system including one or more feature illustrated in and/or described regarding system 100 FIG. 1). Alternatively, or additionally, in some embodiments, selection of lead portion positioning is based on patient data. Where patient data includes, for example, one or more of patient diagnosis, imaging of the patient, patient age, patient weight, data from an implanted device measuring the patient e.g. an IPG.

Alternatively or additionally, in some embodiments, selection of lead portion positioning is automatic, for example, automatically determined based on patient data. Where, in some embodiments, an automatic selection suggestion is presented to a user (e.g. healthcare practitioner) who then uses the suggestion in selecting lead position/s.

In some embodiments, one or more lead is positioned extending into a ventricle e.g. a RV of the heart. In an exemplary embodiment, two leads are positioned within the RV. In some embodiments, one or more of the leads extend from attachment to an IPG (the IPG, for example, including one or more feature as illustrated in and/or described regarding IPG 120 FIG. 1). Alternatively, or additionally, in some embodiments, one or more of the leads are not connected to an IPG (e.g. power source and/or controller circuitry) and, for example, are later connected.

In some embodiments, selecting of a position includes one or more dimension, for example, with respect to one or more landmark e.g. anatomical and/or a marker. In some embodiments, selecting of a position includes one or more dimension of apparatus outside the patient e.g. how far a lead is inserted into the patient e.g. from outside the patient.

In some embodiments, the leads are arranged along a superior-inferior axis (e.g. arranged separated by at least 0.5 cm, or 1 cm, or 2 cm, or lower or higher or intermediate distances). This axis corresponds, in some embodiments, to an axis along which transmission initiated supraventricularly normally travels as it passes through the septum.

Optionally, one or more additional leads are positioned. For example, one or more lead extending into an atrium (e.g. lead 132 FIG. 1) and/or left ventricle LV (e.g. lead 134 FIG. 1).

In some embodiments, leads (e.g. at least two leads) are positioned at initial positions within a heart (e.g. within a right ventricle e.g. as illustrated by leads 102, 104 FIG. 1).

Optionally, in some embodiments, positioning is assisted using one or more measurement. For example, using imaging during the positioning. For example, using measurements (e.g. of cardiac electrical signal/s) collected by electrode/s of the first lead and/or measurements collected by other electrodes within the body and/or heart and/or externally placed sensing electrodes e.g. in contact with a skin surface of the subject.

In some embodiments, a first lead is positioned, position of the first lead is then determined (e.g. using one or more type of measurement e.g. as described in one or more of steps 402-409) before positioning of a second lead, where, in some embodiments, selected and/or planned positioning of the second lead is adjusted, based on the determined positon of the first lead. Alternatively, in some embodiments, both of a first and a second right ventricle leads (e.g. leads 102, 104 FIG. 1) are positioned at the same time.

At 402, measurements are collected using lead electrodes. In some embodiments, one or more type of measurement (e.g. one or more of the measurements described in steps 404-409) are collected for a plurality of cardiac cycles.

At 404, in some embodiments, timing of arrival of a cardiac conduction wave-front at different electrodes is measured.

In some embodiments, measurements are collected of non-stimulated cardiac cycles. Alternatively or additionally, in some embodiments, measurements are collected where the heart is stimulated (for example, paced e.g. atrially paced), for example, at different heart beat rates.

For example, where the heart is stimulated by medication.

In some embodiments, electrical wave propagation within portion/s of the heart are measured. In some embodiments, ventricular wave propagation e.g. through tissue of the septum is measured. In some embodiments, measurements are collected for a plurality of cardiac cycles to provide details of statistical variation of electrical wave propagation e.g. for the individual's heart. Optionally, electrical wave propagation is measured for different heart rates.

In some embodiments, measurement of stimulated (for example, paced e.g. atrially paced) cardiac cycles are used to provide data for "normal" heart beats. In some embodiments, measurements of non-stimulated cardiac cycles are used to provide data for incidence of arrhythmia. Where, in some embodiments, arrhythmia is defined as conduction wave-fronts pasting through the septum but not originating at the atrioventricular node (AV node).

Alternatively or additionally, in some embodiments, normal cardiac propagation is determined using previously collected data e.g. of the patient in question and/or of other subject/s which is optionally tailored to the patient (e.g. by age and/or sex and/or weight and/or medical history).

In some embodiments, relative time of arrival of a cardiac electrical activity wave-front (also herein termed "ventricular event") at a first and at a second electrode is evaluated. In some embodiments, delay between arrival of conduction wave-front is measured for a plurality of cardiac cycles e.g., to enable calculation of a statistical representation of wave-front travel at the sites of electrode implantation.

Optionally, the statistical representation comprises an average delay, and/or a standard deviation of that delay. Optionally, measurements of relative delay are performed at a plurality of heart rates.

In an exemplary embodiment, the ventricular event is a timing of arrival of an R-wave component of a heart electrocardiogram (ECG). The R-wave component has potential advantages for this use insofar as it is relatively large in amplitude and relatively fast; however, any other component of the ongoing cycling heart electrical activity waveform is detected additionally or alternatively to the R-wave.

In some embodiments, an order of detection of a ventricular event between electrodes is used to determine relative distances of the electrodes to the AV node. For example, for designating electrodes as RV and LS for implementation of the method of FIGS. 3A-B. In some embodiments, which electrode of two electrodes is closer to an AV node (e.g. AV node 138 FIG. 1) is determined. In some embodiments, position with respect to the AV node of two electrodes is determined using one or more feature as illustrated in and/or described regarding FIG. 5A.

In some embodiments designation of electrodes as RV and LS (e.g. for the purpose of implementing the method of FIGS. 3A-B) is based on positioning (e.g. determined positioning) of the electrodes, and/or electrical propagation for regular cardiac cycles. In some embodiment the designation is manual, e.g. as selected by a medical practitioner and/or automatically based on preliminary measurements collected using lead electrodes and/or other measurement devices (e.g. external ECG sensor measurements).

Alternatively or additionally, at 406 in some embodiments, tissue impedance is measured between two electrodes. In some embodiments, tissue impedance of heart tissue between electrodes is used to determine the distance between the electrodes. For example, to determine distance between electrodes proximal to and/or in contact with and/or anchored to a septum e.g. electrodes 106, 110, septum 136 FIG. 1. In some embodiments, tissue impedance (e.g. of septum) between the electrodes is measured by injecting current between the electrodes and measuring potential between the electrodes.

In an exemplary embodiment, impedance measurement/s are collected during a refractory period of the cardiac cycle. For example, where the cardiac cycle is monitored, the refractory period for a cycle being determined from measurements of the cycle and/or the refractory period being determined using measurements of previous cardiac cycles. The impedance measurements then being collected in the portion of a cardiac cycle identified as being the refractory period.

Alternatively or additionally, at 407, in some embodiments, the distance between the first and second electrodes is measured by applying electrical stimulation (e.g. a stimulation pulse e.g. current or voltage stimulation e.g. a current or voltage stimulation pulse) at one of the first and second electrodes and measuring decrease in amplitude (and/or timing of arrival) of the pulse at the other of the electrodes. Where the measurements are used to determine the distance between the first and second electrodes.

Alternatively or additionally, at 408 in some embodiments, a distance between the first electrode and the second electrode is measured by stimulation of cardiac tissue (e.g. at one of the electrodes) and measurement of travel time of cardiac tissue action potential induced by the stimulation (e.g. at the other electrode). For example, where electrical stimulation is provided at one of the electrodes and ventricle contractility is measured at the other electrode, characteristics (e.g. delay and/or amplitude) of the ventricle contractility being used to determine distance between the first and second electrodes.

In some embodiments, the same stimulation pulse is used to measure both tissue impedance (e.g. as described in step 406) and to induce cardiac tissue action potential e.g. as described in step 408. In some embodiments, the same stimulation pulse is used to conduct one or more of measurements described in steps 406, 407 and 408.

In some embodiments, one or more of steps 406, 407 and 408 are further described with reference to FIG. 10.

Optionally, at 409, in some embodiments, heart rate measurements are collected e.g. in conjunction with one or more other measurement e.g. one or more of measurements collected at 404, 406, 407, 408. For example, to provide effect of heart rate on measurements. In some embodiments, different heart rates are induced during measurement/s e.g. by pacing e.g. over-pacing and/or stressing the individual (e.g. by physical and/or chemical stressing).

Optionally, at 410, lead and/or electrode position is measured using one or more other measurement modality e.g. imaging e.g. external ECG measurement/s.

At 412, in some embodiments, lead positioning is evaluated using measurement/s collected with the leads at one or more of steps 404-410.

In some embodiments, based on data regarding normal cardiac activity (assumed and/or measured e.g. at step 402), and the ability to vary values of one or more parameter of the windowing algorithm of FIGS. 3A-B, position of electrodes and/or leads is evaluated.

For example, in some embodiments, an optimization process is carried out where, given cardiac activity measurements and flexibility available within the windowing algorithm, a projected incidence of cardiac cycles for which cardiac contractility modulation stimulation is applied, for the electrode position is determined. In some embodiments, a plurality of projected incidences are determined, e.g. for different heart rates.

Where, in some embodiments, duration of one or more of; delay time 302, discrimination window 304, delay time 306, and cardiac contractility modulation stimulation duration 308 of the method of FIGS. 3A-B are adjustable.

In some embodiments, the optimization process includes varying detection of the ventricular event as an input to the windowing algorithm. Where, for example, parameter/s for identifying the R-wave of the cardiac cycles are changed. For example, where a peak of the R-wave is identified, parameter/s of a peak detection algorithm are changed.

For example, in some embodiments, the discrimination window of the method of FIGS. 3A-B is selected, based on wave-front delay measurements collected at step 404. For example, in some embodiments (e.g., for a generally Gaussian distribution of relative delays), the discrimination window duration is selected as a range of delays within ±2, ±3, ±4 or another number of standard deviations of the average delay. Optionally, the window duration (e.g. window 304

FIGS. 3A-B) and/or an offset (delay 302 FIGS. 3A-B) is selected to include all measurements of relative time of arrival, or at least a great majority of the measurements, e.g., at least 99% of measurements, or at least 99.9% of measurements.

Optionally, the selected discrimination window is dynamic e.g. heart rate dependent, and/or selected according to a current heart rate; for example, to account for potential differences in wave-front velocity as a function of heart rate. Heart rate adjustment of the window is optionally performed based on measurements of delays at different heart rates. Optionally, heart rate adjustment of the window is performed based on a standard derived from patient population observations.

In some embodiments, optimization includes one or more requirement. For example, in some embodiments, a minimum delay between detected ventricular events at a first and second electrode is required. In some embodiments, the threshold is a fixed time, where, for example an average and/or a percentage of delays are is required to be above a threshold. In some embodiments, the threshold is 1-8 ms, or 2-5 ms, or 1-4 ms, or 3-4 ms, or about 3 ms, or lower or higher or intermediate durations or ranges.

In some embodiments, a delay between detected events at a first and second electrode is required to be within an allowed time range, for example, 0.5-8 ms, or 0.5-5 ms, or 1-5 ms, or 2-5 ms, or 2-8 ms, or lower or higher or intermediate time durations or ranges.

At 414, in some embodiments, based on the evaluation at 412, one or more lead is repositioned. For example, by advancing and/or retracting lead/s.

In some embodiments, for example, where delay is required to be above a threshold and/or within a range of thresholds, lead/s are repositioned until the desired delay is reached.

In some embodiments, steps 402-414 are repeated a number of times. For example, measurement/s are collected (at one or more of steps 402-410), and a lead is then moved in a first direction. After the movement, measurement/s are collected again, and, if evaluation (e.g. at step 412) indicates that the measurement/s have improved with the movement of the lead, the lead is then moved again in the first direction. In some embodiments, conversely, if the measurement has degraded with movement of the lead, the lead is then moved in a different direction.

At 416, in some embodiments, based on the evaluation at step 412, lead positioning is maintained. For example, by anchoring the leads e.g. to the septum. In some embodiments, apparatus for lead delivery and/or positioning is then withdrawn and/or an IPG is connected and/or implanted.

For example, in some embodiments, an IPG configured to deliver electrical stimulation to one or more electrode of one or more lead is implanted e.g. subcutaneously. The IPG, for example, including one or more feature as illustrated in and/or described regarding IPG 120 FIG. 1. In some embodiments, the IPG is connected to one or more leads previously positioned extending into the heart. In some embodiments, IPG is connected to leads but is not implanted subcutaneously e.g. is connected externally to the patient e.g. with leads extending through a skin surface.

At 420, in some embodiments, determined position of the electrodes is used to determine whether cardiac contractility modulation stimulation is applied e.g. on a per cardiac cycle basis. For example, the determined position is used as an input to one or more feature of the method described in FIG. 3A and FIG. 3B. For example, one or more of a duration of delay time 302, discrimination window 304, delay time 306 and cardiac contractility modulation stimulation duration 308 are selected based on the electrodes position.

At 422, in some embodiments, measurements collected at step 420 are evaluated. For example, periodically. For example, where one or more evaluation parameters are continuously updated.

In some embodiments, duration of a time difference between detected wave-fronts at a first and a second electrode is an evaluation parameter. In some embodiments, evaluation parameters include one or more of median, average, and variability of the time difference.

In some embodiments, timing of ventricular events is evaluated, for one or more cardiac cycle. In some embodiments, for example, for an evaluation time period, a median and/or average and/or variability of one or more timing parameter of sensed ventricular events is evaluated. Where, in some embodiments, timing parameters include a delay between sensing of the ventricular events and/or an order of sensing of ventricular events (e.g. sign of the delay).

In some embodiments, timing of ventricular events is evaluated, based on heart rate associated with the measured ventricular events. For example, heart rate for each cardiac cycle and/or heart rate for a time period. Where the heart rate time period, in some embodiments, is the same or different to the evaluation time period.

For example, in some embodiments, measured time differences between detected wave-fronts at a first and a second electrode are saved with heartrate at the measurement time.

In some embodiments, evaluation includes determining whether a change in evaluation parameter's is associated with a change in cardiac function and/or with a change in measurement electrode and/or lead position within the heart.

In some embodiments, movement of electrode/s and/or lead dislodgement is identified from timing data. For example, in some embodiments, timing changes outside one or more threshold where changes include ordering of ventricular event/s and/or delay between ventricular events with time, optionally with heart rate, an alert is issued indicating potential electrode and/or lead mal-positioning and/or dislodgement. In an exemplary embodiment, if one or more of the average and median delay changes outside an expected range, lead movement (e.g. dislodgement) is identified. Where, in some embodiments, if an average delay changes by more than a threshold e.g. by more than 10%, or more than 20%, or more than 30%, or more than 40%, or lower or higher or intermediate percentages or ranges, lead movement is identified.

Alternatively or additionally, in some embodiments, if a median delay changes by more than a threshold, e.g. by more than 10%, or more than 20%, or more than 30%, or more than 40%, or lower or higher or intermediate percentages or ranges, lead movement is identified.

Optionally, in some embodiments, regular cardiac cycle wave-front propagation is updated and/or re-determined using lead electrode measurements.

At 424, in some embodiments, lead position is updated, e.g. for the purpose of delivering cardiac contractility modulation stimulation.

For example, feedback from step 424 is in some embodiments, an input to step 420. where, in some embodiments, one or more part of the method of determining which cardiac cycles should receive cardiac contractility modulation of FIGS. 3A-B is adjusted, based on lead position (e.g. as updated in step 424). For example, adjusting one or more of delay 302, discrimination window 304, delay 306 FIGS. 3A-B. For example, changing a designation of leads as rv and ls for the method of FIGS. 3A-B, the designation based on lead position, where, in some embodiments, the designation is changed e.g. according to one or more feature illustrated in and/or described regarding the method of FIG. 5A. Potentially, adjustment increases the proportion of cardiac cycles which receive cardiac contractility modulation stimulation.

In some embodiments, position of lead/s and/or electrode/s are evaluated. For example, using electrode measurements (and, optionally additional measurements e.g. imaging). In some embodiments, movement of electrode/s and/or lead dislodgement is identified from measurements e.g. from timing data for events measured by the electrodes. Optionally an alert is initiated, based on the identifying e.g. a lead dislodgement alert.

At 426, in some embodiments, the patient is diagnosed, based on evaluation at step 422. For example, in some embodiments, a cardiac condition is diagnosed using the evaluation. Where, diagnosing, in some embodiments, includes one or more feature as illustrated in and/or described regarding FIG. 5B. Optionally, in some embodiments, diagnosis/es are communicated to a user, for example through transmitter 128 FIG. 1 e.g. to a user interface.

When applying acts 420 and on of FIG. 4, alerts may be generated based on measurements. In one example, an alter is sent if the delay between the two electrodes is not within a desired range, for example, not within 1-4 ms. In some embodiments, an alert is generated each time. Optionally or additionally, an alert is generated based on a number or frequency of the event. Optionally or additionally, a report is generated periodically, for example, once a week.

In some embodiments of the invention, alerts are transmitted, for example, using a wireless connection, to a remote monitoring site (e.g., or a cloud location). Optionally or additionally, the transmission is to a local device, such as a cellular telephone (e.g., using BlueTooth or other local wireless connectivity), which may send the received data on, optionally after processing. Optionally or additionally, data regarding such alerts is downloaded using a local device, for example, a device programmer, optionally as a report and/or a summary.

In some embodiments of the invention, measurements include delay measurements and/or impedance measurements, at one or both of the electrodes and/or between electrodes. Such impedance measurements may be useful to indicate a quality of contact between an electrode and cardiac tissue (e.g., dislodgment) and/or damage to electrode and/or lead.

Referring specifically to act 420, in some embodiments of the invention cardiac contractility modulation stimulation is optionally applied to both electrodes at the same or overlapping times (e.g., in a same cardiac cycle and a same or overlapping time windows within a cardiac cycle), for example, having an overlap of between 10 and 99%, for example, between 10% and 30%, 30% and 70% and/or 70% and 99%.

Exemplary Lead Selection

FIG. 5A is a method of electrode selection for implementing methods of controlling an implantable pulse generator, according to some embodiments of the invention.

At 500, in some embodiments, ventricular events passing a first and a second electrode (e.g. electrodes 106, 110 FIG. 1) are identified. Where identifying, in some embodiments, is according to one or more feature as described regarding step 404 FIG. 4.

In some embodiments, a time difference between identified ventricular events is determined from measurements. In some embodiments, an ordering of sensed ventricular events between the first and second electrodes is determined using electrode measurement data. In some embodiments, the order is determined from a sign of the delay between sensed ventricular events at the different electrodes, e.g. in a cardiac cycle. In some embodiments, determining is for measurements collected from a plurality, n, of cardiac cycles.

At 502, in some embodiments, a ventricular event order prevalence is determined e.g. for the n cardiac cycles. Where, in some embodiments, order prevalence is, for a time period, which electrode detects the ventricular event first, the majority of the time.

Alternatively or additionally to measuring at 500, n cardiac cycles and determining order prevalence for n cycles, in some embodiments, determining of order is continuous and/or order prevalence is continuously updated e.g. as measurements are collected.

At 504, based on the determined ventricular event order prevalence, RV and LS are designated. For example, for the purpose of determining when cardiac contractility modulation stimulation should be applied e.g. according to one or more feature as illustrated in and/or described regarding FIG. 3A and/or FIG. 3B.

In some embodiments, RV and LS electrodes are designated periodically. For example, steps 500-504 being repeated periodically, e.g. for a set number of cardiac cycles and/or time duration. For example, once an hour, 1-5 times a day, once a day, once every other day, or lower or higher or intermediate frequencies or ranges of frequencies of repeating of steps 500-504.

Additionally or alternatively, in some embodiments, steps 500-504 are repeated upon a user input where a user requests an evaluation and/or manually designates electrode order.

Additionally or alternatively, in some embodiments, steps 500 and 502 are performed continuously, and step 504 is performed upon detection of a change. For example, upon change in the majority order prevalence, for a time period (e.g. a pre-determined time period). For example, upon a change in variability of the order prevalence (e.g. above a threshold).

Exemplary Monitoring

FIG. 5B is a method of monitoring, according to some embodiments of the invention.

At 501, in some embodiments, for example as described elsewhere within this document, relative timing (e.g. a time difference) between detection of a conduction waveform at different electrodes is determined from measurements collected with the electrodes. In some embodiments, the time difference is measured for a plurality of cardiac cycles. Optionally, in some embodiments, heart rate is measured.

At 503, optionally, in some embodiments, bound/s for normal time differences and/or value/s for normal time differences, optionally with heart rate are determined using measurements collected at 501. Where, for example, measured time differences over time and/or with heart rate are used to provide expected value/s and/or range/s for the particular subject. In some embodiments, a value for normal time differences is provided by a statistical representation of measured normal time differences. For example, one or more of mean, median, standard deviation, variance, skew, kurtosis, extrema, maximum, minimum, range, second moment.

Alternatively, in some embodiments, statistical representation value/s and/or normal bounds are fixed and/or estimated using patient data (e.g. age, diagnosis).

In some embodiments normal range/s and/or expected average values and/or statistical representation value/s are determined using fixed or estimated values which are then adjusted using measurements.

In some embodiments, normal ranges and/or value/s (e.g. of statistical representation/s) are updated periodically, using measurements.

In some embodiments, measurements from cardiac cycles which are determined to be ineligible for cardiac contractility modulation (and/or other treatment and/or stimulation), for example, as described elsewhere in this document are excluded from those used to determine normal range/s and/or value/s (e.g. of statistical representation/s).

In some embodiments, the statistical representation is one which describes variation of the time difference over a time period.

At 505, in some embodiments, measured time differences are compared with normal value/s and/or range/s. In some embodiments, comparison is for individual cardiac cycles. Alternatively or additionally, in some embodiments, comparison is of statistical representation value/s of the measured time differences for at time period. For example, in some embodiments, comparison is of average (e.g. median) values for a time period. Where, in some embodiments, averages are determined using time difference values for like heart rates.

At 507, in some embodiments, based on the comparison performed at step 505, the subject is diagnosed.

In some embodiments, if variation of the time difference increases with heartrate, potential induced ischemia and/or increased arrhythmia risk is diagnosed.

In some embodiments, if, at high heart rates, variability of the time difference increases, potential induced ischemia and/or increased arrhythmia risk is diagnosed. Where, in some embodiments, potential induced ischemia is diagnosed for heart rates over 100 bpm, or over 110 bpm, or over 120 bpm, or lower or higher or intermediate heart rates, if, at these elevated heart rates, a statistical representation of the time difference indicates increased variation in the time difference (e.g. over a threshold).

As noted with respect to FIG. 4, such measurements and/or analysis thereof may be outputted form the implanted device or from a controller thereof, for example, as an alert and/or a report and/or raw or processed data.

Exemplary Discrimination of Cardiac Conduction Patterns

Referring back now to FIGS. 3A-B. In some embodiments, FIGS. 6A-D illustrate how the algorithm e.g. as described regarding and/or illustrated in FIGS. 3A-B is used to differentiate between normal sinus rhythm and arrhythmia e.g. to provide cardiac contractility modulation only for normal cardiac cycles.

FIGS. 6A-D are schematic illustrations of discrimination of conduction patterns passing through a ventricular septum 636, according to some embodiments of the invention.

Shown in each of FIGS. 6A-8D are leads 602, 604 positioned within heart 616, and sensing (electrode) positions 611A, 612A. Also shown are different estimates of an intraseptal conduction vector 615, which varies in direction and length depending on the apparent direction and speed of wave-front conduction between sensing positions 611A and 612A.

In the timelines at the bottom of each of FIGS. 6A-6D, marks 611, 612 represent the times at which a conduction wave-front reaches sensing position 611A and 612A, respectively. Time range 613, in some embodiments, represents a discrimination window (which, in some embodiments, includes one or more feature of discrimination window FIG. 3A-B).

In some embodiments of the invention, a first division of normal and abnormal sinus rhythms may comprise orthodromic (e.g., FIGS. 6A, 6C) and antidromic (e.g., FIG. 6B, 6D) conduction through the ventricular septum.

Referring to FIG. 6A, normal sinus rhythm, as well as some supraventricular tachycardias (SVTs), have cardiac conduction wave-front vectors travelling to the ventricle in an orthodromic direction (i.e., conduction vector 615 from wave-front position 610A toward wave-front position 610B) through the normal conduction apparatus (Bundle of His and Purkinje Fibers) within the ventricular septum. Where SVTs with orthodromic directions include potentially, one or more of:

atrial tachycardia, atrial flutter, atrial fibrillation, atrioventricular nodal re-entrant tachycardia (AVNRT), and orthodromic Wolf-Parkinson-White atrioventricular re-entrant tachycardia (Orthodromic WPW-AVRT).

True-ventricular tachycardias, on the other hand, are conducted through the conduction system in an antidromic direction, and/or produce disturbances within the conduction system itself. For example, in FIG. 6B, conduction is antidromic from wave-front position 610C toward wave-front position 610D. In FIG. 6D, conduction comprises an antidromic component as the wave-front moves between wave-front position 610H and wave-front position 610G. Conduction in FIG. 6C is orthodromic, but moves from wave-front position 610E toward wave-front position 610F, rather than originating supraventricularly.

The timelines of FIGS. 6A-6D represent example/s of how the method of FIGS. 3A-B is implemented, in some embodiments of the invention.

In each of FIGS. 6A-6D, mark 611 falls either within (FIG. 6A) or outside of (FIGS. 6B-6D) discrimination window 613.

When mark 611 falls within discrimination window 613, in some embodiments, this is considered an indication that cardiac contractility modulation stimulation should be applied.

FIGS. 7A-E and FIGS. 8A-E illustrate timing of ventricular event detection for different conduction vectors and different electrode positions with respect to the conduction vectors. In some embodiments, one or more the figures illustrates how optimization of the windowing algorithm and/or position of electrodes is used to optimize application of cardiac contractility modulation.

FIGS. 7A-D are simplified schematic illustrations of sensing of cardiac conduction wave-fronts, according to some embodiments of the invention.

In some embodiments, wave-fronts illustrated by arched dashed lines pass through septal tissue 750. Where, normal wave-fronts originate at an AV node 738 and travel in an inferior direction away from AV node 738 through septal tissue 736.

In some embodiments, FIGS. 7A-C illustrate passage of different wave-fronts, for a first electrode spatial configuration.

In FIG. 7A propagation is that of a "normal" conduction wave-front 750, which emanates from AV node 738 travels in an inferior direction through septum tissue 736.

FIG. 7B, also illustrates, in some embodiments, a normal conduction wave-front, but where a direction of travel of wave-front 752 is at a slight angle to a vector 760 connecting electrodes 703, 704.

FIG. 7C, in some embodiments, illustrates a wave-front of an arrhythmia, e.g. where the wave-front does not originate at AV node 738.

FIG. 7D, in some embodiments, illustrates a normal wave-front but for a different electrode spatial configuration than illustrated in FIGS. 7A-D.

FIG. 7E is a simplified schematic illustration of timelines of sensed ventricular events, according to some embodiments of the invention.

In some embodiments, FIG. 7E illustrates timing for the schematic illustrations of FIGS. 7A-D.

Of note is how the timeline of sensed arrhythmia as illustrated in FIG. 7C is the same as the timeline for FIG. 7E where one of the electrodes has moved e.g. dislodged from the position illustrated in FIGS. 7A-C.

FIGS. 8A-D are simplified schematic illustrations of sensing of cardiac conduction wave-fronts, according to some embodiments of the invention.

FIG. 8E is a simplified schematic illustration of timing of a sensed ventricular events, according to some embodiments of the invention.

In some embodiments, FIGS. 8A-D illustrate sensing of propagating cardiac electrical waves with different directions for a second electrode spatial configuration. In some embodiments, FIG. 8E illustrates timelines of sensed ventricular events corresponding to illustrations of FIGS. 8A-D.

If cardiac wave-fronts pass more frequently in a direction through the septum e.g. towards the left of septum 836 (directions herein referring to directions with respect FIGS. 8A-D), in some embodiments electrodes are positioned correspondingly, for example, as illustrated in FIGS. 8A-D. Potentially, positioning electrodes to a configuration corresponding to more wave-fronts potentially increases the proportion of normal wave-fronts (and cardiac cycles) for which cardiac contractility modulation stimulation is applied.

However, referring to FIG. 8C, an angled electrode configuration as illustrated in FIGS. 8A-C provides a smaller time difference between delays for normal cardiac cycles than would the electrode configuration e.g. of FIGS. 7A-D.

However, referring to FIG. 8D, the angled electrode configuration potentially reduces the proportion of cardiac cycles in different direction to the direction identified as more prevalent. FIG. 9 is a schematic illustration of three-sensor discrimination of conduction patterns passing through a ventricular septum, according to some embodiments of the invention.

In some embodiments, methods of positioning electrode/s and/or adjusting of a windowing algorithm to produce optimal cardiac contractility modulation stimulation (e.g. as described elsewhere in this document) are used when more than two electrodes are used to sense cardiac conduction waveforms.

Two remaining forms of arrhythmia—antidromic Wolf-Parkinson-White atrioventricular re-entrant tachycardia (antidromic WPW-AVRT) and Wolf-Parkinson-White atrial fibrillation (WPW-AF)—comprise SVTs which potentially cannot be discriminated from true ventricular tachycardias through an analysis of the conduction speed and direction of the depolarization wave-front sweeping the ventricular septum alone.

Shown in FIG. 9 in addition to leads 102, 104 positioned in a septum of heart 916 is a third lead 103, positioned in another ventricular region. Lead 103 is shown entering heart 916 through the same blood vessel (e.g., the superior vena cava) as leads 104, 102; however, it is optionally routed from another direction. To sensing (electrode) positions 911A, 912A, is thereby added a third sensing position 914A, corresponding to the position of the electrode of lead 103. In some embodiments, lead 103 is an LV lead, for example as used in cardiac resynchronization therapy (RCT); e.g., a lead passing along the coronary sinus. In some embodiments, lead 103 is a lead placed in the apex of the left atrium.

In this instance, the estimate of intraseptal conduction vector 915 appears indistinguishable from normal orthodromic conduction, and indeed mark 911 on the timeline for FIG. 9 falls within discrimination window 913. This could potentially result in a determination that any concurrent tachycardia is supraventricular in origin.

However, in some embodiments, detection of a conduction wave-front passing through sensing position 914A results in the activation of a predetermined suppression window 913B.

Suppression window 913B suppresses the defibrillation discrimination function of discrimination window 913, with the result that defibrillation is not suppressed, even though mark 911 falls within the period which would otherwise result in the prevention of delivery of a defibrillation shock.

The suppression window 913B, in some embodiments, is long enough to cover the time it takes for conduction to pass circuitously between wave-front position 910J and wave-front position 910K, but not so long that it would potentially suppress discrimination of SVT (e.g., about 100-250 msec, or another suitable duration). Optionally, suppression window 913B begins after delay 913A (e.g., of about 1-50 msec). The delay 913A, in some embodiments, is set to be long enough, e.g., so that an atrially originating wave-front arriving first at sensing position 914A and then, a few milliseconds later, at e.g., sensing position 912A is not confused with a ventricular origin of wave-front initiation. In some embodiments, suppression window 913B may itself be suppressed, for example, if there is a detection of a conduction wave-front passing sensing position 912A just before, or within a sufficiently short time period after a wave-front passes position 915A.

Exemplary Measurement of Electrode Position, Using Electrical Stimulation

FIG. 10 is a simplified schematic showing a stimulation signal 1046 and a measurement signal 1048, according to some embodiments of the invention.

In some embodiments, an electrical stimulation pulse 1050 is applied within a heart, for example, to heart tissue (e.g. at one of electrodes 106, 110, FIG. 1).

In some embodiments, distance between electrodes is determined using measurements of pulse 1050. For example, using an electrical measurement signal e.g. measured at another septum electrode, for example the second of two septal electrodes e.g. if the stimulation pulse is applied at electrode 106 then the measurement signal is measured at electrode 110 (referring to electrodes 106, 110, FIG. 1).

In some embodiments, measurement is of a single resulting pulse 1052, for example, where a second pulse 1054 does not occur.

For example, when the stimulation pulse is applied during the refractory period, where, in some embodiments, a second pulse associated with simulation of cardiac contractility in cardiac tissue does not result or results to a minimal extent.

In some embodiments, after pulse 1052 a second measurement pulse 1054 is observed. For example, when stimulation pulse 1050 is applied not during the refractory period of the cardiac cycle. Delay between measurement pulses 1052, 1054, and/or the delay between pulses 1050 and 1054 in some embodiments, is associated with difference in speed of travel of electrical pulses through tissue as opposed to speed of travel cardiac contractility stimulated by pulse 1050. In some embodiments, position of electrodes (e.g.

106, 110 FIG. 1) is additionally or alternatively determined using measurement of second pulse 1054.

In some embodiments, timing of one or both of pulses 1052, 1054 is used to determine position of the electrodes. Alternatively or additionally, in some embodiments, amplitude of one or both of pulses 1052, 1054, optionally with respect to an amplitude of the applied pulse 1050 is used to determine position of the electrodes.

In some embodiments, for example, as pulse 1052 in some embodiments is measured almost instantaneously with injection of pulse 1050, amplitude of pulse 1052 (e.g. difference between amplitude of pulse 1050 and pulse 1052) is used to determine distance between the electrodes.

In some embodiments, delay between pulse 1050 and/or pulse 1042 and pulse 1054 is used to determine distance between the electrodes.

General

It is expected that during the life of a patent maturing from this application many relevant cardiac stimulation technologies will be developed and the scope of the term cardiac stimulation is intended to include all such new technologies a priori.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for cardiac stimulation comprising:
an implantable controller, said controller configured to carry out the method of:
  receiving measurements from at least two electrodes positioned within the heart;
  designating, based on said measurements, one electrode of said at least two electrodes as a first electrode, and another electrode of said at least two electrodes as a second electrode;
  generating a signal to cause application of cardiac contractility modulation stimulation to said heart, if a ventricular event is detected at said first electrode and later, after a suitable time delay, at said second electrode.

2. The system according to claim 1, wherein said designating comprises monitoring said measurements for a plurality of cardiac cycles and designating said first electrode for an electrode of said at least two electrodes which senses a ventricular event first for more than half of said cardiac cycles.

3. The system according to claim 1, wherein said measurements comprise cardiac electrical measurement signals from said at least two electrodes which are positioned at a right ventricle septum.

4. The system according to claim 1, wherein said designating comprises identifying, from said measurements, timing of arrival of a cardiac action potential wave-front at said at least two electrodes.

5. The system according to claim 1, wherein said at least two electrodes includes a first and a second electrode positioned at a septum and at least one additional electrode, where said measurements include measurement of potential at said first and said second electrode each with respect to said additional electrode.

6. The system according to claim 1, wherein said delay is at least 1 ms and at most 4 ms.

7. The system according to claim 1, configured to generate an alert if said delay is not within a desired range.

8. The system according to claim 1, configured to perform impedance measurements at and/or between said two electrodes.

9. The system according to claim 1, wherein said system is configured to perform said applying at both of said electrodes, overlapping in time.

10. The system according to claim 1, wherein said system is configured to perform said applying at both of said electrodes in a same cardiac cycle, at least in part, not overlapping in time.

11. The system according to claim 1, comprising changing previous designating in response to periodic measurements from the electrodes.

12. The system according to claim 1, wherein designating comprises designating at least one electrode as right ventricle (RV), and at least one electrode as left ventricle (LS).

13. A method of monitoring comprising:
monitoring, over time, a time difference between arrival of a cardiac action potential wave-front at two electrodes, each positioned at a different point on a heart;
based on said monitoring one or more of:
  designating relative position of the two electrodes, based on said time difference, for determination of which cardiac cycles should receive cardiac contractility modulation stimulation.

14. The method according to claim 13, wherein said two electrodes are each positioned at a different point on a heart septum.

15. The method according to claim 13, wherein said monitoring comprises, for a plurality of cardiac cycles:
receiving cardiac electrical measurement signals from said two electrodes;
identifying timing of arrival of a cardiac action potential wave-front at each of said two electrodes from said measurement signals;
determining a time difference between arrival of said cardiac action potential wave-front at said two electrodes, for a plurality of cardiac cycles; and
generating, from time differences determined for said plurality of cardiac cycles, a statistical representation of said time differences.

16. The method according to claim 13, wherein said determining comprises determining a sign of said time difference.

17. The method according to claim 15, wherein said wherein said statistical representation comprises a propensity of which electrode of said two electrodes senses said cardiac action potential wave-front first.

18. The method according to claim 13, wherein said designating comprises designating the electrode for which more than half of the wave-fronts are sensed first as being closer to an a trioventricular node.

19. The method according to claim 15, wherein said method further comprises diagnosing a cardiac condition based on said determination; and wherein said diagnosing comprises comparing said statistical representation with a threshold.

20. The method according to claim 15, comprising receiving heart rate measurements, for said plurality of cardiac cycles; and wherein said generating comprises generating a statistical representation of said time differences with respect to heart rate;

wherein if said statistical representation indicates increase in variation of time differences with increased heart rate, diagnosing potential induced ischemia; wherein said increase heart rate includes statistical representations of said time differences for heart rates over a threshold rate;

wherein if said statistical representation indicates increase in variation of time differences for one or more heart rate, diagnosing potential cardiac arrhythmia.

21. The method according to claim 15, wherein said statistical representation of said time differences is a median of said time differences for a time period.

22. The method according to claim 21, wherein if said median deviates by more than a threshold value over a time period of less than a minute, lead dislodgement is identified.

23. The method according to claim 13, comprising selecting, during implantation of the electrodes, positioning of lead portions of each of the two electrodes based on the monitored time difference.

24. A system for cardiac stimulation comprising:

an implantable controller, said controller configured to carry out the method of:

receiving measurements from at least two electrodes positioned within the heart;

designating, from said measurements, a first electrode of said at least two electrodes and a second electrode of said at least two electrodes;

wherein said designating comprises monitoring said measurements for a plurality of cardiac cycles and designating said first electrode for an electrode of said at least two electrodes which senses a ventricular event first for more than half of said cardiac cycles;

applying cardiac contractility modulation stimulation to said heart if a ventricular event is detected at said first electrode and then at said second electrode after a suitable time delay.

25. A system for cardiac stimulation comprising:

an implantable controller, said controller configured to carry out the method of:

receiving measurements from at least two electrodes positioned within the heart;

designating, from said measurements, a first electrode of said at least two electrodes and a second electrode of said at least two electrodes;

wherein said designating comprises identifying, from said measurements, timing of arrival of a cardiac action potential wave-front at said at least two electrodes;

applying cardiac contractility modulation stimulation to said heart if a ventricular event is detected at said first electrode and then at said second electrode after a suitable time delay.

* * * * *